(12) United States Patent
Chen et al.

(10) Patent No.: US 8,110,703 B2
(45) Date of Patent: Feb. 7, 2012

(54) RETINOID DERIVATIVE AND PHARMACEUTICAL COMPOSITION AND USE THEREOF

(75) Inventors: Feihu Chen, Anhui (CN); Jingbo Shi, Anhui (CN); Yuan Wang, Anhui (CN); Jun Li, Anhui (CN); Juan Shen, Anhui (CN); Jingjing Ruan, Anhui (CN); Fanrong Wu, Anhui (CN)

(73) Assignees: Anhui Medical University, Hefei, Anhui (CN); Anhui New Star Pharmaceutical Development Co., Ltd., Hefei, Anhui (CN)

( * ) Notice: Subject to any disclaimer, the term of this patent is extended or adjusted under 35 U.S.C. 154(b) by 0 days.

(21) Appl. No.: 12/994,862

(22) PCT Filed: May 31, 2009

(86) PCT No.: PCT/CN2009/000605
§ 371 (c)(1),
(2), (4) Date: Nov. 29, 2010

(87) PCT Pub. No.: WO2009/143715
PCT Pub. Date: Dec. 3, 2009

(65) Prior Publication Data
US 2011/0077298 A1 Mar. 31, 2011

(30) Foreign Application Priority Data

May 30, 2008 (CN) .......................... 2008 1 0110794

(51) Int. Cl.
C07C 69/74 (2006.01)
C07C 321/00 (2006.01)
C07C 229/00 (2006.01)
C07C 233/00 (2006.01)
C07C 327/00 (2006.01)
A01N 37/10 (2006.01)
A01N 37/18 (2006.01)
A61K 31/165 (2006.01)

(52) U.S. Cl. .............. 560/128; 560/15; 560/17; 560/38; 560/43; 564/161; 564/162; 564/163; 558/257; 514/532; 514/613; 514/617

(58) Field of Classification Search ........................ None
See application file for complete search history.

(56) References Cited

FOREIGN PATENT DOCUMENTS
WO PCT/CN2009/000605  8/2009
WO 2010036404 * 4/2010

OTHER PUBLICATIONS

Shen et al., Chinese Chemical Letters (2009), 20(7), 809-811.*
ScienceDirect online abstract of Shen et al., Chinese Chemical Letters (2009), 20(7), 809-811.*

(Continued)

*Primary Examiner* — Karl J Puttlitz
(74) *Attorney, Agent, or Firm* — Global IP Services; Tianhua Gu

(57) ABSTRACT

The invention relates to a retinoid derivative and pharmaceutical composition and use thereof. The compound of the invention is capable of preventing or treating hematological tumors, such as acute leukemia, chronic leukemia, multiple myeloma and lymphoma, solid tumors, such as liver cancer, rectal cancer, mammary cancer and esophagus cancer, and skin disorders, such as psoriasis and acne.

8 Claims, 5 Drawing Sheets

OTHER PUBLICATIONS

Database Caplus Chemical Abstracts Service, Columbus, Ohio, US; Database Accession No. 2009:920554, Abstract of Shet et al.: "Synthesis and anti-tumor activity of retinoic acid derivatives." Zhongguo Xinyao Zazhi (2009), 18(11), 1050-1053.*

Database Caplus Chemical Abstracts Service, Columbus, Ohio, US; Database Accession No. 2009:1115865, Abstract of Yao et al.: "Effects of N-(3-trifluoromethyl-phenyl)-retinamide on proliferation and apoptosis of human pulmonary adenocarcinoma A549 cells." Anhui Yike Daxue Xuebao (2008), 43(6), 674-678.*

Database Caplus Chemical Abstracts Service, Columbus, Ohio, US; Database Accession No. 2009:1444998, Abstract of Wang et al.: "Effects of 4-amino-2-trifluoromethyl-phenyl retinoate on expression of RAR.alpha. and EGFR in lung cancer cells." Anhui Yike Daxue Xuebao (2009), 44(2), 249-253.*

Ullmann's Encyclopedia of Industrial Chemistry, Copyright © 2002 by Wiley-VCH Verlag GmbH & Co. KGaA, pp. 1-51.*

Kirk-Othmer Encyclopedia of Chemical Technology Copyright © 2002 by John Wiley & Sons, Inc., pp. 95-147, Article Online Posting Date: Aug. 16, 2002.*

Rouhi, "The Right Stuff, from research and development to the clinic, getting drug crystals right is full of pitfalls", Chemical & Engineering News, Feb. 24, 2003, pp. 32-35.*

D.L. Newton et al., Cancer Research 1980; 40, 1980, pp. 3413-3425.*

* cited by examiner

A

B

C

D

E

F

G

H

I

J

RETINOID DERIVATIVE AND PHARMACEUTICAL COMPOSITION AND USE THEREOF

CROSS REFERENCE TO RELATED PATENT APPLICATION

The present application is the US national stage of PCT/CN2009/000605 filed on May 31, 2009 which claims the priority of the Chinese patent application No. 200810110794.1 filed on May 30, 2008, which application is incorporated herein by reference.

FIELD OF THE INVENTION

The invention relates to a retinoid derivative and pharmaceutically salt thereof and pharmaceutical composition prepared therefrom. The invention further relates to a preparation method and use of the retinoid derivative and pharmaceutically salt thereof. The invention belongs to the chemical and pharmaceutical fields.

BACKGROUND OF THE INVENTION

Cancer threatens the lives of all human beings greatly. According to the statistics from the WHO, cancer kills an estimated 5 million people around the world every year, so the prevention and therapy for cancer are onerous tasks. The drug therapy is one of three main therapies for cancer. The conventional therapies for malignant tumours by chemical drugs focus on killing tumour cells directly or indirectly, resulting in certain lethality to normal cells, obvious toxic and side effects, and great restriction to such cytotoxic drugs in therapeutic effect and application due to the drug resistance of the tumour cells. Since Friend, et al., discovered that mouse erythroleukemia cells induced by DMSO can be differentiated to synthesize hemoglobin in 1971, people have gradually recognized that malignant cells can be 'reversed' by using differentiation inducers to return to normal cells, which arouses the interest and attention of scholars. With the in-depth research on tumour pathogenesis, the induction of differentiation therapy has become a new breakthrough in the tumour therapeutics. The induction of differentiation is a phenomenon that malignant tumour cells, under the actions of differentiation inducers in vitro and in vivo, differentiate and reverse to normal cells or close to normal cells. This therapy focuses on returning the tumours back rather than killing them directly, thereby curing them finally. The discovery of effective differentiation inducers will change the former treatment modes of mainly killing the tumour cells, and form a new therapy of mainly controlling and adjusting the biological behaviours of the tumour cells, thereby implementing the cure of tumours finally. Particularly in recent 20 years, with the tremendous development of molecular biology of tumour and its technology, scientists have achieved fruitful outcomes in the field of drug research on inducing malignant tumour cells to differentiate and discovered hundreds of compounds with differentiation functions, many of which have been in the clinic tests of stages I and II and a few of which, such as retinoic acid, have been used as differentiation inducers for the clinic tumour treatment and prevention, with certain therapeutic effect, therefore, the research and application of differentiation inducers open a wide way for tumour drugs and their pharmaceutical research.

Retinoic acid and retinoids thereof are a range of vitamin A derivatives of over 4000 kinds, including retinoic acid, vaminic acid, viaminate, natural vitamin A, etc. Retinoid compounds are widely used for the therapy of skin disorders, such as keratosis and photoage, however, remarkably for the prevention and therapy of some malignant tumours, such as mammary cancer, skin cancer, cervical cancer and leukaemia. Scientific researchers widely and deeply research all-trans retinoic acid and 9-cis retinoic acid of such compounds. The two compounds have the functions of resisting keratosis and hyperplasia and improving the normal differentiation of epidermal cells by involving in the proliferation and differentiation of regulatory cells, interfering the occurrence of tumours by inhibiting the activity of ornithine dehydrogenase, and are capable of directly inhibiting the synthesis of sebum and the proliferation of sebaceous gland cells to reduce the secretion of sebum (You Lei, Yan Huanglin, Retinoid Compounds and Receptors Thereof and Research Development of Psoriasis; Medical Recapitulate 2007, 13 (06), 466-467). Since 1988, Shanghai Retinoic Acid Association first used all-trans retinoic acid (ATRA) for the induction of differentiation therapy of human acute promyelocytic leukaemia with remarkable therapeutic effect and complete remission rate of 86% based on 5-year clinic summary. At present, ATRA has been used in the treatment of malignant tumours, such as acute promyelocytic leukaemia and oral leukoplakia and become one of the preferred drugs for the treatment of leukaemia (Evans T R, Kaye S B. Br J Cancer, 1999, 80 (1-2): 1-9) 9-cis retinoic acid has the therapeutic effect equivalent to that of ATRA but less side effect, hopefully used as a clinic drug. The structures of common retinoid compounds are as follows:

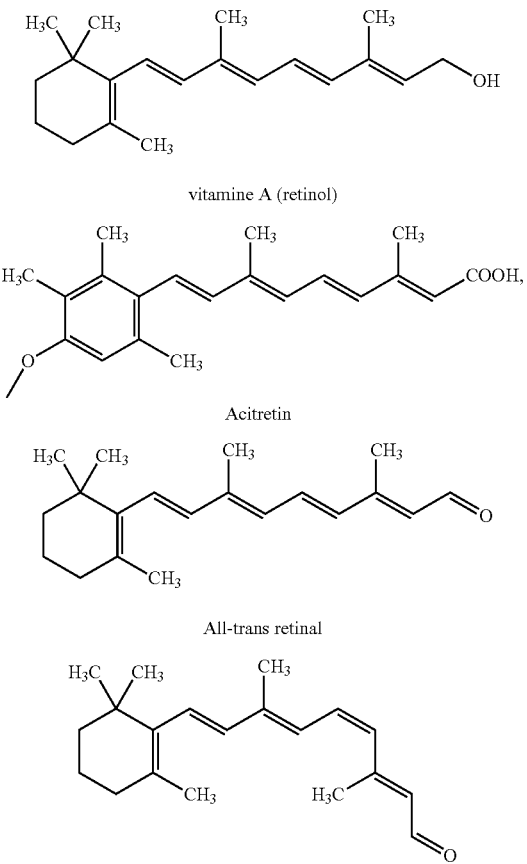

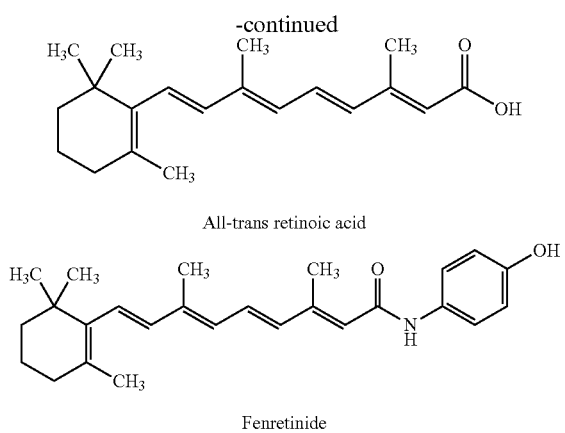

All-trans retinoic acid

Fenretinide

However, with increasingly wide application of retinoic acid, the untoward effects occurred often caused by ATRA are as follows: 1, damage of skin and mucous membrane; 2, untoward effects of digestive system with high incidence rate, such as nausea, vomiting, anorexia and distended upper abdomen; 3, untoward effects of nervous system, such as headache, papilledema and increased cerebrospinal pressure, during the treatment of patients by ATRA; 4, untoward effects of bone, joint and muscle normally caused by ATRA; 5, increased leukocyte count with the incidence rate of about 30% during the treatment of APL by ATRA, reported abroad; and, 6, retinoic acid syndrome (RA-RS), the main danger during the treatment of APL by ATRA, with the main manifestations of fever and difficulty in breathing and other symptoms and physical signs of increased weight, distal limb edema, hydrothorax or pericardial effusion, and paroxysmal hypotension and pulmonary interstitial infiltration seen from chest radiograph. In addition, ATRA can cause carpal tunnel syndrome, serious heart damage, hyperlipidemia, hyperammonemia and other untoward effects (Zhao Huanyu; Untoward Effects of All-trans Retinoic Acid; Chinese Pharmaceutical Journal 1998 33 (7): 440-441), greatly limiting the application of drugs. Meanwhile, fast developed drug resistance and high recurrence rate are still two obstacles affecting the long-term therapeutic effect. With the further application in clinic, people found that ATRA can form drug resistance and make the remission of patients suffering recurrence more difficult. Thus, it is necessary to improve the therapeutic effect, widen the clinic application range and reduce the untoward effect of drugs. Therefore, a great number of structure modification jobs for the retinoid drugs are carried out home and abroad.

Xu Shiping, et al., designed and synthesized a series of retinoic acid derivatives for improving the performance of retinoid compounds (Acta Pharmaceutica Sinica (1981), 16 (9), 678-86), in which viaminate (RI) and vaminic acid (RII) have better effects in anti-carcinogenesis and the like, with lower toxicity, thereby being suitable for the cancer chemoprophylaxis and the treatment of precancerous lesion. Du Congzhi, et al., found that viaminate (RI) and vaminic acid (RII) have low toxicity, compared with the toxicities of retinoid compounds, such as viaminate (RI), vaminic acid (RII), retinoic acid, etretinate and isotretinoin, which indicates that they are suitable for the application of the treatment of precancerous lesion (Acta Pharmaceutica Sinica 17: 333-337 (1982)). An invention, application No.: 97116602.1, discloses a retinamide coumarin compound and preparation method thereof and pharmaceutical compositions having the same.

There are also lots of reports related to the research on retinoids abroad. For example, isotretinoin and acitretin have been in the market as skin drugs. The structure modification of terminal polar groups of retinoic acid is focused on the oxyacylation and azoacylation. For example, Kyoko Nakagawa-Goto, et al., adopted the condensate of retinoic acid and taxane for enhancing the therapeutic effect of drugs (Kyoko Nakagawa-Goto, Koji Yamada, et al., Antitumor agents. 258. Syntheses and evaluation of dietary antioxidant-taxoid conjugates as novel cytotoxic agents, Bioorganic & Medicinal Chemistry Letters 17 (2007) 5204-5209), and, Gholam H. Hakimelahi, et al., used monoclonal antibodies capable of combining with the specificities of surface antigens of tumour cells as carriers to transport β-lactamase, after which the retinoic acid prodrug (a compound obtained by connecting ATRA to the C-3 position of a cephalosporin) was administrated and catalyzed by the β-lactamase at the tumour cells to release pharmacophoric groups in the C-3 position, thereby selectively killing the tumour cells. In-vitro experiment found that the joint use of the compound (5) and β-lactamase has greater inhibition to the proliferation of mammary cancer tumour cell MCF7 than that of the compound (5) (Hakimelahi G H, Ly T W, Yu S F, et al. Design and synthesis of a cephalosporin-retinoic acid prodrug activated by a monoclonal antibody-β-lactamase conjugate [J]. Bioorg Med Chem, 2001, 9(8): 2139-2147). Stefano Manfredini, et al., covalently condensed retinoic acid with Ara-A, Ara-C and 3 (2H)-Furanone, in which some compounds have strong inhibition to the growth of cells (Stefano Manfredini, Daniele Simoni, Roberto Ferroni, et al. Retinoic Acid Conjugates as Potential Antitumor Agents: Synthesis and Biological Activity of Conjugates with Ara-A, Ara-C, 3 (2H)-Furanone, and Aniline Mustard Moieties, J. Med. Chem. 1997, 40, 3851-38), but the modifications to these structures are to joint the corresponding drugs and exert the functions of the drugs, with the defects of large molecular weight and uncertain stability and drug targets due to the joint of two drugs, thereby possibly not being used for drug application. So micromolecular compounds ought to be used as substrates for terminal carboxyl acylation.

U.S. Pat. No. 4,190,594 discloses esterification and amidation of a series of retinoic acids for the prevention and treatment of the damage caused by UV irradiation, in which, fenretinide (4-HPR), is often used for the treatment of various skin disorders and currently as a drug for the prevention and treatment of many tumours for the evaluation (Soo-Jong U M, a Youn-Ja KWON, et al. Synthesis and Biological Activity of Novel Retinamide and Retinoate Derivatives, Chem. Pharm. Bull. 52 (5)501-506 (2004)). Fenretinide (4-HPR) is the selective agonist for RAR-β and RAR-γ. According to the researches in recent years, fenretinide is different from the conventional retinoid compounds that it has weaker induction of differentiation, strong action of improving the apoptosis of tumour cells, and lower toxicity than other retinoid compounds, for long-term use with low incidence rate of drug resistance and for single or joint use with other chemical therapy drugs for anti-tumour. In recent years, some researches abroad showed that fenretinide has the direct inhibition effect to many different solid tumours and has been in the stage of clinic experiment, with incomplete known anti-tumour action mechanisms. The present researches found that the possible mechanisms of fenretinide include proliferation inhibition to tumour cells, differentiation improvement, apoptosis initiation and influence on other signalling pathways, and the apoptosis-inducing biochemical pathway of fenretinide is so complex. Meanwhile, retinoic acid receptor dependence and retinoic acid receptor independence were reported, and the latter can improve the generation of reactive oxygen species (ROS) and neuropeptide, etc. In addition, the fenretinide can inhibit angiogenesis and HIV, resist rheumatism, treat psoriasis and the like. Therefore, fenretinide becomes one focus in the current research. But, during the clinic application, its main disadvantage is low bioavailability. The researches indicated that, when the dosage of a patient is 200 mg/day, the plasma concentration of the patient is lower than 1 μM, while the effective concentration required to generate apoptosis in vivo is 101 μM, therefore, it is necessary to increase the administration dosage or synthesize derivatives with better clinic effect. The recently synthesized derivatives are obtained by hydroxylation and carboxylation or methoxy-substitution and the like to the aniline structure. But only partial compounds in these derivatives show better bioactivities (Clifford J. L., Sabichi A. L., Zou C., Yang X., Steele V. E., Kelloff G. J., Lotan R., Lippman S. M., Cancer Epidemiol. Biomarkers Prev., 10, 391-395 (2001); Sun S. Y., Yue P., Kelloff G. J., Steele V. E., Lippman S. M., Hong W. K., Lotan R., Cancer Epidemiol. Biomarkers Prey., 10, 595-601 (2001)). Soo-Jong U M, et al., modified the structure of 4-HPR and obtained a series of compounds having high cytotoxicity and better water solubility. The main method is to bond sodium butyrate having anticancer activity to retinoic acid by p-aminophenol to generate 4-BPRE, a butyryl aminophenyl ester of retinoic acid. The molecular pharmacology experiment shows that the compound has the dual anti-tumour activities of sodium butyrate and retinoic acid both (Um S J, Kwon Y J, Han H S, et al. Synthesis and biological activity of novel retinamide and retinoate derivatives [J]. Chem Pharm Bull, 2004, 52 (5): 501-506; Um S J, Han H S, Kwon Y J, et al. In vitro antitumor potential of 4-BPRE, a butyryl aminophenyl ester of retinoic acid: role of the butyryl group [J]. Oncol Rep, 2004, 11 (3): 719-726).

SUMMARY OF THE INVENTION

The invention aims to provide a retinoid derivative with a novel structure.

The technical scheme is as follows.

The compound of the invention is a retinoid derivative with formula (I),

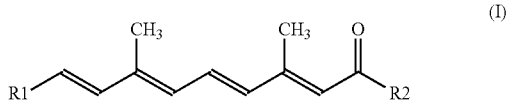

(I)

or an isomer, enantiomer, racemate, diastereomer mixture, racemic mixture, solvate, polymorph or pharmaceutically acceptable salt thereof, wherein: R1 represents a structure of formula (II) or formula (III), and R2 represents a structure of formula (IV);

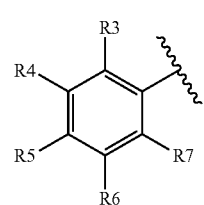

(II)

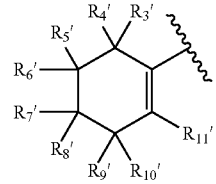

(III)

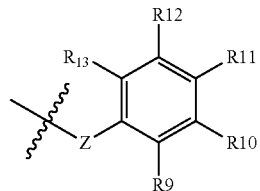

(IV)

∼∼∼represents bonding positions;
R3-R7 are same or different, each independently selected from hydrogen, nitro, halogen, amino, acyl, sulfonamide, carboxy, carboxylate, amide, nitrile, hydroxy, carbamyl, thiourea, aminomethyl, cyano, substituted or unsubstituted lower alkyl, substituted or unsubstituted lower alkenyl, substituted or unsubstituted lower alkynyl, substituted or unsubstituted lower alkoxy, substituted or unsubstituted lower alkylamino, substituted or unsubstituted lower alkylthio, substituted or unsubstituted lower alkylsulfo, substituted or unsubstituted lower alkylamide, substituted or unsubstituted lower aliphatic alkenyloxy, substituted or unsubstituted lower aliphatic alkynyloxy, substituted or unsubstituted aliphatic cycloalkyl, substituted or unsubstituted heterocycloalkyl, substituted or unsubstituted aryl, substituted or unsubstituted heteroaryl, substituted or unsubstituted aryloxy, substituted or unsubstituted heteroaryloxy, substituted or unsubstituted arylcarbonyl, substituted or unsubstituted heteroarylcarbonyl, substituted or unsubstituted aryloxycarbonyl, substituted or unsubstituted heteroaryloxycarbonyl, substituted or unsubstituted arylamino, substituted or unsubstituted heteroarylamino, substituted or unsubstituted arylthio, or substituted or unsubstituted heteroarylthio;
R3'-R11' are same or different, each independently selected from hydrogen, nitro, halogen, amino, acyl, sulfonamide, carboxy, carboxylate, amide, nitrile, hydroxy, carbamyl, thiourea, aminomethyl, cyano, substituted or unsubstituted lower alkyl, substituted or unsubstituted lower alkenyl, substituted or unsubstituted lower alkynyl, substituted or unsubstituted lower alkoxy, substituted or unsubstituted lower alkylamino, substituted or unsubstituted lower alkylthio, substituted or unsubstituted lower alkylsulfo, substituted or unsubstituted lower alkylamide, substituted or unsubstituted lower aliphatic alkenyloxy, substituted or unsubstituted lower aliphatic alkynyloxy, substituted or unsubstituted aliphatic cycloalkyl, substituted or unsubstituted heterocycloalkyl, substituted or unsubstituted aryl, substituted or unsubstituted heteroaryl, substituted or unsubstituted aryloxy, substituted or unsubstituted heteroaryloxy, substituted or unsubstituted arylcarbonyl, substituted or unsubstituted heteroarylcarbonyl, substituted or unsubstituted aryloxycarbonyl, substituted or unsubstituted heteroaryloxycarbonyl, substituted or unsubstituted arylamino, substituted or unsubstituted heteroarylamino, substituted or unsubstituted arylthio, or substituted or unsubstituted heteroarylthio;
R9-R13 are same or different, each independently selected from haloalkyl, haloalkoxy, hydrogen, nitro, halogen, amino, acyl, sulfonamide, carboxy, carboxylate, amide, nitrile, hydroxy, carbamyl, thiourea, aminomethyl, cyano, substituted or unsubstituted lower alkyl, substituted or unsubstituted lower alkenyl, substituted or unsubstituted lower alkynyl, substituted or unsubstituted lower alkoxy, substituted or unsubstituted lower alkylamino, substituted or unsubstituted lower alkylthio, substituted or unsubstituted lower alkylsulfo, substituted or unsubstituted lower alkylamide, substituted or unsubstituted lower aliphatic alkenyloxy, substituted or unsubstituted lower aliphatic alkynyloxy, substituted or unsubstituted aliphatic cycloalkyl, substituted or unsubstituted heterocycloalkyl, substituted or unsubstituted aryl, substituted or unsubstituted heteroaryl, substituted or unsubstituted aryloxy, substituted or unsubstituted heteroaryloxy, substituted or unsubstituted arylcarbonyl, substituted or unsubstituted heteroarylcarbonyl, substituted or unsubstituted aryloxycarbonyl, substituted or unsubstituted heteroaryloxycarbonyl, substituted or unsubstituted arylamino, substituted or unsubstituted heteroarylamino, substituted or unsubstituted arylthio, or substituted or unsubstituted heteroarylthio;

Z is O, S or NR14 with R14 being selected from hydrogen, substituted or unsubstituted lower alkyl, substituted or unsubstituted lower alkenyl, substituted or unsubstituted lower alkynyl, substituted or unsubstituted aliphatic cycloalkyl, substituted or unsubstituted heterocycloalkyl, substituted or unsubstituted aryl, and substituted or unsubstituted heteroaryl; and the condition is that at least one of R9-R13 is haloalkyl or haloalkoxy.

Preferably, in the retinoid derivative, R3 and R7 are same or different, and respectively are substituted or unsubstituted lower alkyl; R4 and R6 are same or different, each selected from hydrogen, substituted or unsubstituted lower alkyl, substituted or unsubstituted lower alkoxy, substituted or unsubstituted lower aliphatic alkenyloxy, nitro, amino, lower alkyl substituted amino, substituted or unsubstituted N-heterocyclyl; and R5 is substituted or unsubstituted lower alkoxy; and the lower means containing 1-5 carbon atoms, and the substituents during the substitution are selected from nitro, halogen, amino, acyl, sulfonamide, carboxy, carboxylate, amide, nitrile, hydroxy, carbamyl, thiourea, aminomethyl or cyano.

Most preferably, in the retinoid derivative, R5 is methoxy and R6 is hydrogen, when R3, R7 and R4 are methyl.

Preferably, in the retinoid derivative, R3' and R4' are same or different, and respectively are substituted or unsubstituted lower alkyl; R5' to R10' are same or different, each selected from hydro, substituted or unsubstituted lower alkyl, substituted or unsubstituted lower alkoxy, substituted or unsubstituted lower aliphatic alkenyloxy, nitro, amino, lower alkyl substituted amino, substituted or unsubstituted N-heterocyclyl; and R8' is hydro, substituted or unsubstituted lower alkoxy, substituted or unsubstituted lower alkenyl, substituted or unsubstituted lower alkoxy; and the lower means containing 1-5 carbon atoms, and the substituents during the substitution are selected from nitro, halogen, amino, acyl, sulfonamide, carboxy, carboxylate, amide, nitrile, hydroxy, carbamyl, thiourea, aminomethyl or cyano.

Most preferably, in the retinoid derivative, R3' and R4' are methyl, R5' to R10' are hydrogen, and R11' is methyl.

Preferably, in the retinoid derivative, R9 to R13 are same or different, each independently selected from trifluoromethyl, trifluoromethoxy, hydrogen, halogen, hydroxy, substituted or unsubstituted lower alkyl, substituted or unsubstituted lower alkoxy, substituted or unsubstituted lower aliphatic alkenyloxy, carboxylic acid, carboxylate, amide, nitrile, nitro, amino, substituted or unsubstituted lower alkyl substituted amino or N-heterocyclyl, provided that one of R9 to R13 is trifluoromethyl or trifluoromethoxy.

The term, halogen, includes fluorine, chlorine, bromine and iodine.

The lower means containing 1 to 8 carbon atoms, preferably, 1 to 5 carbon atoms.

The group can contain substituents or not. When substituted, the substituents have no limit and can contain one or more substituents preferably selected from nitro, halogen, amino, acyl, sulfonamide, carboxy, carboxylate, amide, nitrile, hydroxy, carbamyl, thiourea, aminomethyl or cyano, and the like.

Those skilled in the art will understand that the compound with formula (I) possibly contains a chiral centre. If so, it can be in the form of an enantiomer. The pure optical isomer, enantiomer mixture, diastereomer mixture, racemic mixture, pharmaceutically acceptable salt and solvate of the compound fall within the scope of the invention.

The compound of the invention can be further in the form of a polymorph, such as amorphous form and crystalline form. All the crystal forms of the compound of the invention fall within the scope of the invention.

Preferably, the invention relates to the following retinoid derivatives:

(4-trifluoromethylphenyl)-(all-trans)-3,7-dimethyl-9-(2,6,6-trimethyl-1-cyclohexen-1-yl)-2,4,6,8-nonatetraenoate;
(3-trifluoromethylphenyl)-(all-trans)-3,7-dimethyl-9-(2,6,6-trimethyl-1-cyclohexen-1-yl)-2,4,6,8-nonatetraenoate;
(2-trifluoromethylphenyl)-(all-trans)-3,7-dimethyl-9-(2,6,6-trimethyl-1-cyclohexen-1-yl)-2,4,6,8-nonatetraenoate;
(4-trifluoromethylphenyl)-(all-trans)-3,7-dimethyl-9-(2,6,6-trimethyl-1-cyclohexen-1-yl)-2,4,6,8-nonatetraenoic acid amide;
(3-trifluoromethylphenyl)-(all-trans)-3,7-dimethyl-9-(2,6,6-trimethyl-1-cyclohexen-1-yl)-2,4,6,8-nonatetraenoic acid amide;
(4-amino-3-trifluoromethylphenyl)-(all-trans)-3,7-dimethyl-9-(2,6,6-trimethyl-1-cyclohexen-1-yl)-2,4,6,8-nonatetraenoate;
(4-amino-2-trifluoromethylphenyl)-(all-trans)-3,7-dimethyl-9-(2,6,6-trimethyl-1-cyclohexen-1-yl)-2,4,6,8-nonatetraenoate;
(4-trifluoromethoxyphenyl)-(all-trans)-3,7-dimethyl-9-(2,6,6-trimethyl-1-cyclohexen-1-yl)-2,4,6,8-nonatetraenoate;
(3-trifluoromethoxyphenyl)-(all-trans)-3,7-dimethyl-9-(2,6,6-trimethyl-1-cyclohexen-1-yl)-2,4,6,8-nonatetraenoate;
(4-trifluoromethoxyphenyl)-(all-trans)-3,7-dimethyl-9-(2,6,6-trimethyl-1-cyclohexen-1-yl)-2,4,6,8-nonatetraenoic acid amide;
(3-trifluoromethoxyphenyl)-(all-trans)-3,7-dimethyl-9-(2,6,6-trimethyl-1-cyclohexen-1-yl)-2,4,6,8-nonatetraenoic acid amide;
(4-hydroxy-3-trifluoromethylphenyl)-(all-trans)-3,7-dimethyl-9-(2,6,6-trimethyl-1-cyclohexen-1-yl)-2,4,6,8-nonatetraenoic acid amide;
(4-hydroxy-2-trifluoromethylphenyl)-(all-trans)-3,7-dimethyl-9-(2,6,6-trimethyl-1-cyclohexen-1-yl)-2,4,6,8-nonatetraenoic acid amide;
(3-trifluoromethylphenyl)-(all-trans)-9-(4-methoxy-2,3,6-trimethylphenyl)-3,7-dimethyl-2,4,6,8-nonatetraenoate;
(2-trifluoromethylphenyl)-(all-trans)-9-(4-methoxy-2,3,6-trimethylphenyl)-3,7-dimethyl-2,4,6,8-nonatetraenoate;
(4-trifluoromethylphenyl)-(all-trans)-9-(4-methoxy-2,3,6-trimethylphenyl)-3,7-dimethyl-2,4,6,8-nonatetraenoate;
(3-trifluoromethoxyphenyl)-(all-trans)-9-(4-methoxy-2,3,6-trimethylphenyl)-3,7-dimethyl-2,4,6,8-nonatetraenoic acid amide;

(2-trifluoromethoxyphenyl)-(all-trans)-9-(4-methoxy-2,3,6-trimethylphenyl)-3,7-dimethyl-2,4,6,8-nonatetraenoic acid amide;

(4-amino-3-trifluoromethylphenyl)-(all-trans)-9-(4-methoxy-2,3,6-trimethylphenyl)-3,7-dimethyl-2,4,6,8-nonatetraenoate;

(4-amino-2-trifluoromethylphenyl)-(all-trans)-9-(4-methoxy-2,3,6-trimethylphenyl)-3,7-dimethyl-2,4,6,8-nonatetraenoate;

(4-trifluoromethoxyphenyl)-(all-trans)-9-(4-methoxy-2,3,6-trimethylphenyl)-3,7-dimethyl-2,4,6,8-nonatetraenoate;

(3-trifluoromethoxyphenyl)-(all-trans)-9-(4-methoxy-2,3,6-trimethylphenyl)-3,7-dimethyl-2,4,6,8-nonatetraenoate;

(3-trifluoromethoxyphenyl)-(all-trans)-9-(4-methoxy-2,3,6-trimethylphenyl)-3,7-dimethyl-2,4,6,8-nonatetraenoic acid amide;

(2-trifluoromethoxyphenyl)-(all-trans)-9-(4-methoxy-2,3,6-trimethylphenyl)-3,7-dimethyl-2,4,6,8-nonatetraenoic acid amide;

(4-trifluoromethoxyphenyl)-(all-trans)-9-(4-methoxy-2,3,6-trimethylphenyl)-3,7-dimethyl-2,4,6,8-nonatetraenoic acid amide;

(4-hydroxy-3-trifluoromethylphenyl)-(all-trans)-9-(4-methoxy-2,3,6-trimethylphenyl)-3,7-dimethyl-2,4,6,8-nonatetraenoic acid amide; or (4-hydroxy-2-trifluoromethylphenyl)-(all-trans)-9-(4-methoxy-2,3,6-trimethylphenyl)-3,7-dimethyl-2,4,6,8-nonatetraenoic acid amide.

The retinoid derivative of formula (I) can be prepared from the following steps by using retinoid acid or etretin as a raw material.

A. Retinoid acid or etretin is reacted with phosphorus trichloride, and the resultant product is reacted with the corresponding aromatic amine derivatives or phenol derivatives to obtain the corresponding derivatives.

B. Retinoid acid or acitretin is reacted with the corresponding aromatic amine derivatives or phenol derivatives in the presence of N,N-dicyclohexylcarbodiimide (DDC) and 4-dimethylaminopyridine (DMAP) to obtain the corresponding derivatives.

C. Retinoid acid or acitretin is reacted with the corresponding aromatic amine derivatives or phenol derivatives in the presence of N,N-dicyclohexylcarbodiimide (DDC) and 4-dimethylaminopyridine (DMAP) p-toluene sulphonate to obtain the corresponding derivatives.

The preparation methods above are briefly illustrated in the following reaction diagrams:

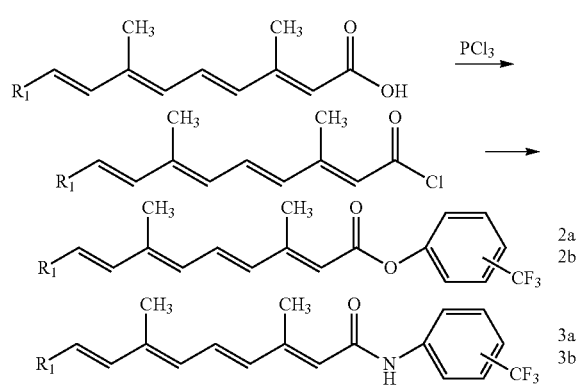

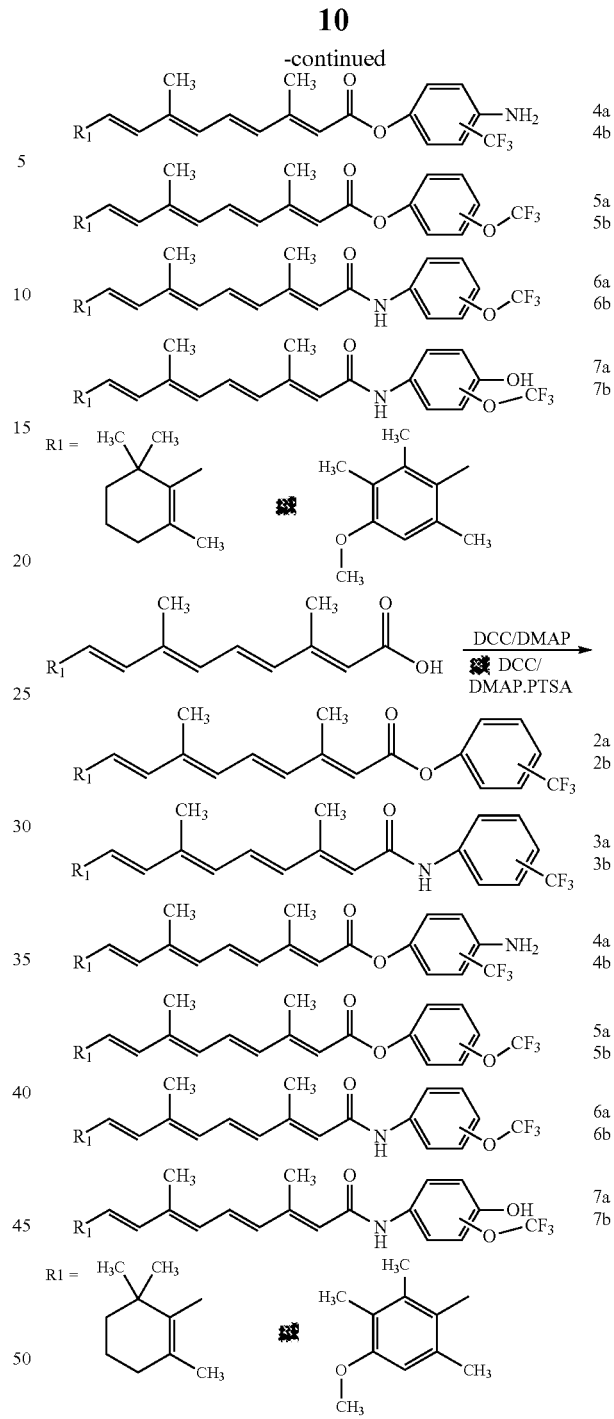

The retinoid derivative of the invention is an unreported new compound. The synthesis methods for their analogs have been reported a lot, mainly, including acryl chloridization, DCC, DCC/DMAP and other methods, which can synthesize the new compounds of the invention.

Furthermore, the following compounds (formulas c-01 to c-15 and d-01 to d-15) synthesized by the invention are those in the examples. The preparation methods are as follows.

General synthesis for compounds of c formula series

In a reaction flask, retinoic acid, polysubstituted aniline or phenol containing trifluoromethyl or trifluoromethoxyl, 4-dimethylaminopyridine (DMAP), dichloromethane of 5 ml, and dichloromethane solution of DCC are added, stirred at the room temperature for standing overnight; and saturated ammonium chloride solution is added to stop the reaction, followed by extraction by dichloromethane, washing by water, drying by anhydrous sodium sulphate, concentration, column chromatography (petroleum ether: 60-90° C.), fraction collection and concentration to obtain the products.

General Synthesis for Compounds of d Formula Series

In a reaction flask, etretin, polysubstituted aniline or phenol containing trifluoromethyl or trifluoromethoxyl, 4-dimethylaminopyridine (DMAP), dichloromethane of 5 ml, and dichloromethane solution of DCC are added, stirred at the room temperature for standing overnight; and saturated ammonium chloride solution is added to stop the reaction, followed by extraction by dichloromethane, washing by water, drying by anhydrous sodium sulphate, concentration, column chromatography (petroleum ether: 60-90° C.), fraction collection and concentration to obtain the products.

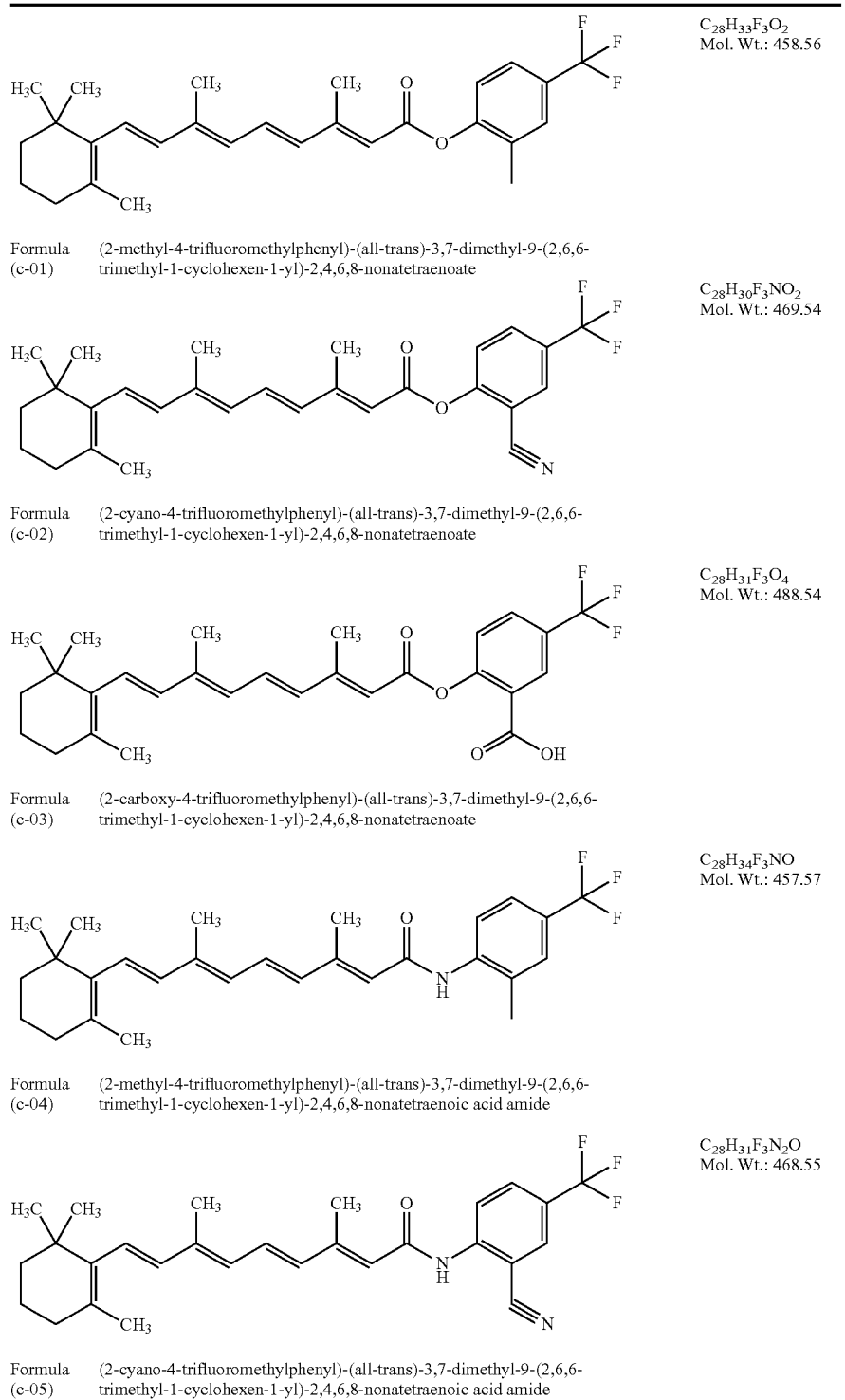

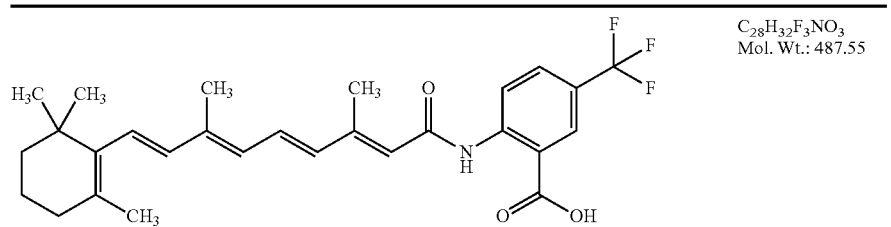

Formula (c-06) (2-carboxy-4-trifluoromethylphenyl)-(all-trans)-3,7-dimethyl-9-(2,6,6-trimethyl-1-cyclohexen-1-yl)-2,4,6,8-nonatetraenoic acid amide $C_{28}H_{32}F_3NO_3$
Mol. Wt.: 487.55

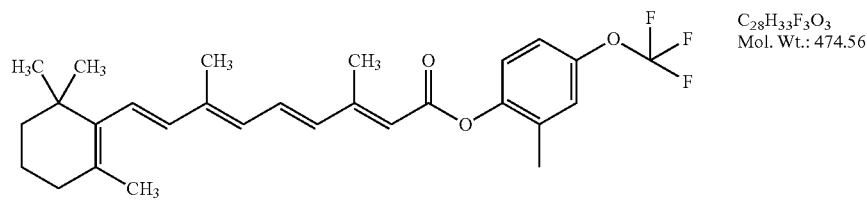

Formula (c-07) (2-methyl-4-trifluoromethoxyphenyl)-(all-trans)-3,7-dimethyl-9-(2,6,6-trimethyl-1-cyclohexen-1-yl)-2,4,6,8-nonatetraenoate $C_{28}H_{33}F_3O_3$
Mol. Wt.: 474.56

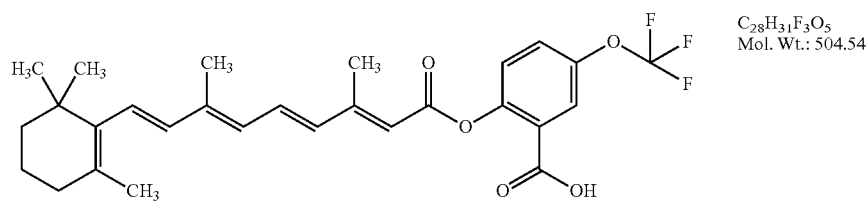

Formula (c-08) (2-carboxy-4-trifluoromethoxyphenyl)-(all-trans)-3,7-dimethyl-9-(2,6,6-trimethyl-1-cyclohexen-1-yl)-2,4,6,8-nonatetraenoate $C_{28}H_{31}F_3O_5$
Mol. Wt.: 504.54

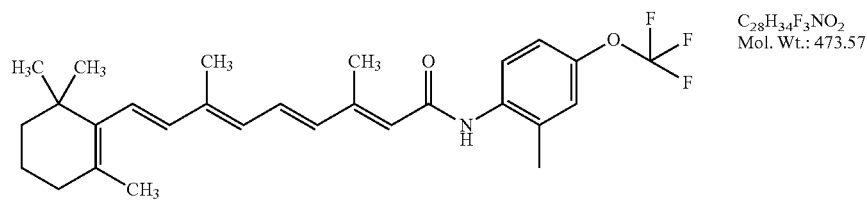

Formula (c-09) (2-methyl-4-trifluoromethoxyphenyl)-(all-trans)-3,7-dimethyl-9-(2,6,6-trimethyl-1-cyclohexen-1-yl)-2,4,6,8-nonatetraenoic acid amide $C_{28}H_{34}F_3NO_2$
Mol. Wt.: 473.57

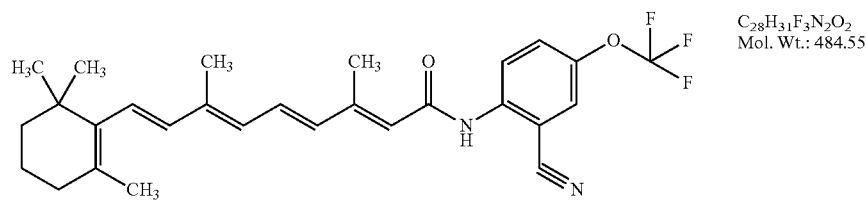

Formula (c-10) (2-cyano-4-trifluoromethoxyphenyl)-(all-trans)-3,7-dimethyl-9-(2,6,6-trimethyl-1-cyclohexen-1-yl)-2,4,6,8-nonatetraenoic acid amide $C_{28}H_{31}F_3N_2O_2$
Mol. Wt.: 484.55

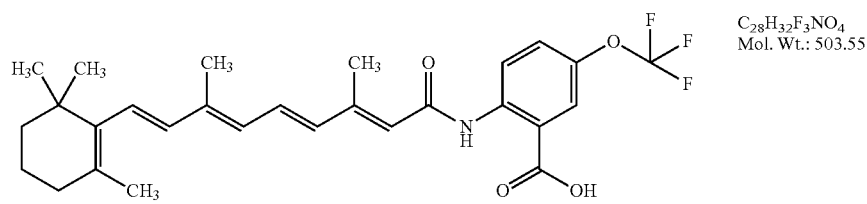

Formula (c-11) (2-carboxy-4-trifluoromethoxyphenyl)-(all-trans)-3,7-dimethyl-9-(2,6,6-trimethyl-1-cyclohexen-1-yl)-2,4,6,8-nonatetraenoic acid amide $C_{28}H_{32}F_3NO_4$
Mol. Wt.: 503.55

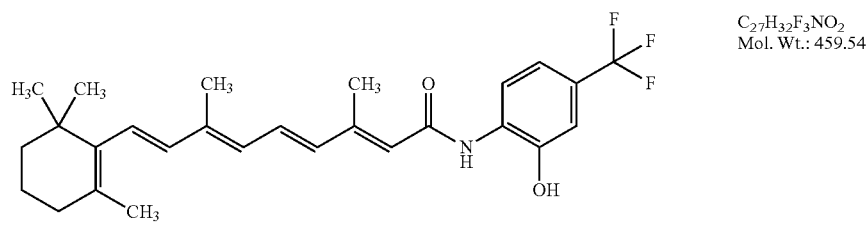

C₂₇H₃₂F₃NO₂
Mol. Wt.: 459.54

Formula (c-12) (2-hydroxy-4-trifluoromethylphenyl)-(all-trans)-3,7-dimethyl-9-(2,6,6-trimethyl-1-cyclohexen-1-yl)-2,4,6,8-nonatetraenoic acid amide

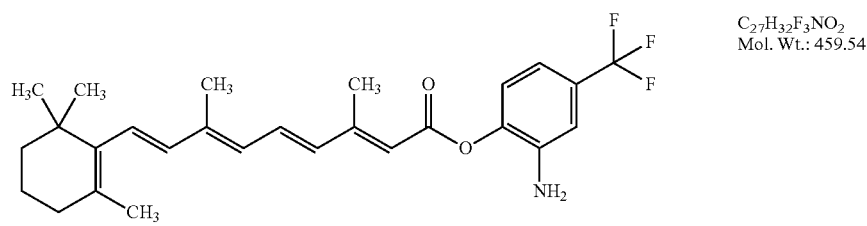

C₂₇H₃₂F₃NO₂
Mol. Wt.: 459.54

Formula (c-13) (2-amino-4-trifluoromethylphenyl)-(all-trans)-3,7-dimethyl-9-(2,6,6-trimethyl-1-cyclohexen-1-yl)-2,4,6,8-nonatetraenoate

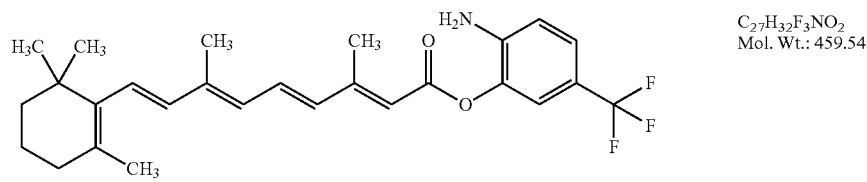

C₂₇H₃₂F₃NO₂
Mol. Wt.: 459.54

Formula (c-14) (2-amino-5-trifluoromethylphenyl)-(all-trans)-3,7-dimethyl-9-(2,6,6-trimethyl-1-cyclohexen-1-yl)-2,4,6,8-nonatetraenoate

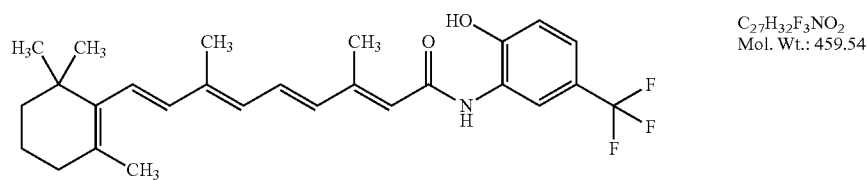

C₂₇H₃₂F₃NO₂
Mol. Wt.: 459.54

Formula (c-15) (2-hydroxy-5-trifluoromethylphenyl)-(all-trans)-3,7-dimethyl-9-(2,6,6-trimethyl-1-cyclohexen-1-yl)-2,4,6,8-nonatetraenoic acid amide

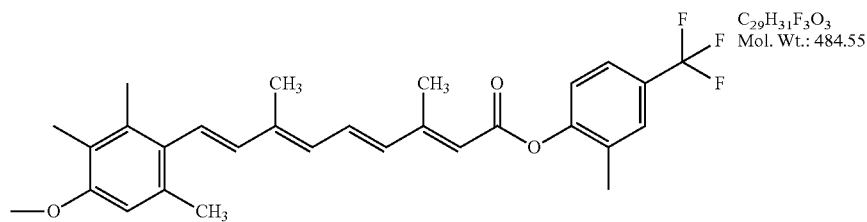

C₂₉H₃₁F₃O₃
Mol. Wt.: 484.55

Formula (d-01) (2-methyl-4-trifluoromethylphenyl)-(all-trans)-9-(4-methoxy-2,3,6-trimethylphenyl)-3,7-dimethyl-2,4,6,8-nonatetraenoate -continued

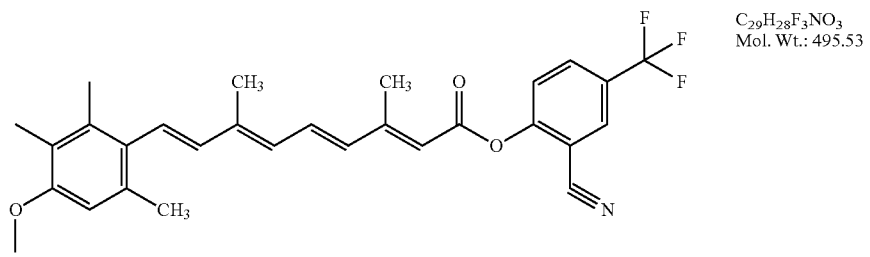

C$_{29}$H$_{28}$F$_3$NO$_3$
Mol. Wt.: 495.53

Formula (d-02)  (2-cyano-4-trifluoromethylphenyl)-(all-trans)-9-(4-methoxy-2,3,6-trimethylphenyl)-3,7-dimethyl-2,4,6,8-nonatetraenoate

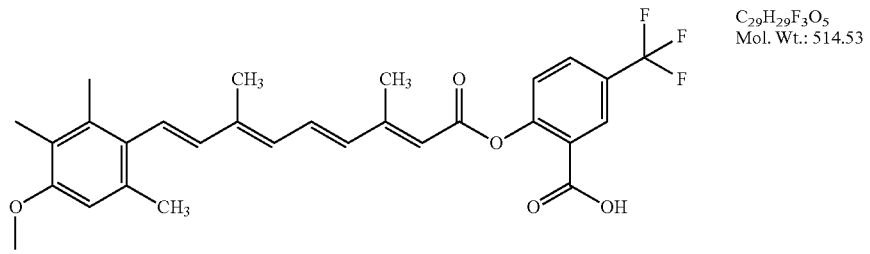

C$_{29}$H$_{29}$F$_3$O$_5$
Mol. Wt.: 514.53

Formula (d-03)  (2-carboxy-4-trifluoromethylphenyl)-(all-trans)-9-(4-methoxy-2,3,6-trimethylphenyl)-3,7-dimethyl-2,4,6,8-nonatetraenoate

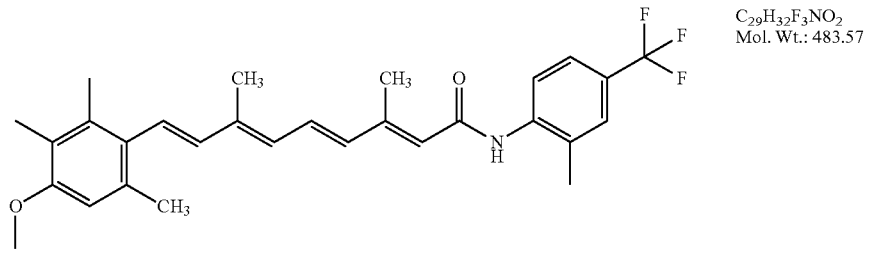

C$_{29}$H$_{32}$F$_3$NO$_2$
Mol. Wt.: 483.57

Formula (d-04)  (2-methyl-4-trifluoromethylphenyl)-(all-trans)-9-(4-methoxy-2,3,6-trimethylphenyl)-3,7-dimethyl-2,4,6,8-nonatetraenoic acid amide

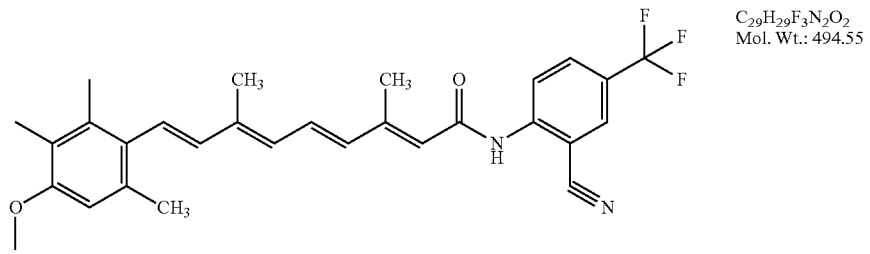

C$_{29}$H$_{29}$F$_3$N$_2$O$_2$
Mol. Wt.: 494.55

Formula (d-05)  (2-cyano-4-trifluoromethylphenyl)-(all-trans)-9-(4-methoxy-2,3,6-trimethylphenyl)-3,7-dimethyl-2,4,6,8-nonatetraenoic acid amide

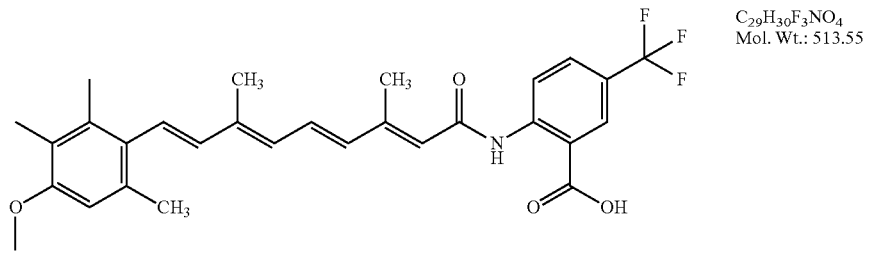

C$_{29}$H$_{30}$F$_3$NO$_4$
Mol. Wt.: 513.55

Formula (d-06)  (2-carboxy-4-trifluoromethylphenyl)-(all-trans)-9-(4-methoxy-2,3,6-trimethylphenyl)-3,7-dimethyl-2,4,6,8-nonatetraenoic acid amide -continued

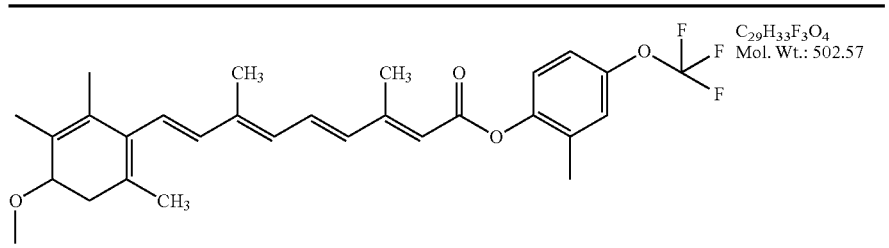

Formula (d-07) (2-methyl-4-trifluoromethoxyphenyl)-(all-trans)-9-(4-methoxy-2,3,6-trimethylphenyl)-3,7-dimethyl-2,4,6,8-nonatetraenoate

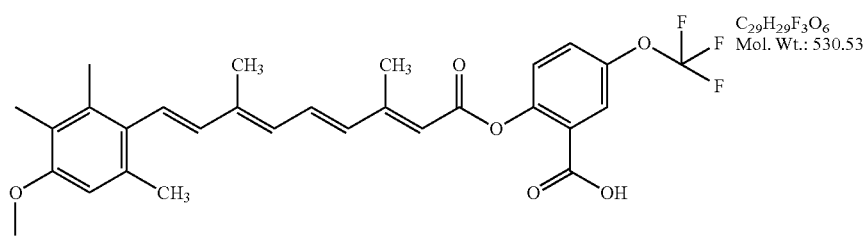

Formula (d-08) (2-carboxy-4-trifluoromethoxyphenyl)-(all-trans)-9-(4-methoxy-2,3,6-trimethylphenyl)-3,7-dimethyl-2,4,6,8-nonatetraenoate

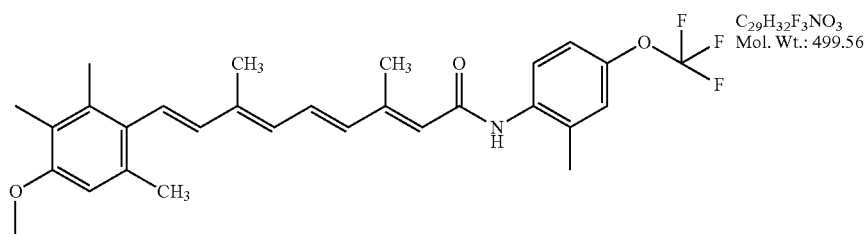

Formula (d-09) (2-methyl-4-trifluoromethoxyphenyl)-(all-trans)-9-(4-methoxy-2,3,6-trimethylphenyl)-3,7-dimethyl-2,4,6,8-nonatetraenoic acid amide

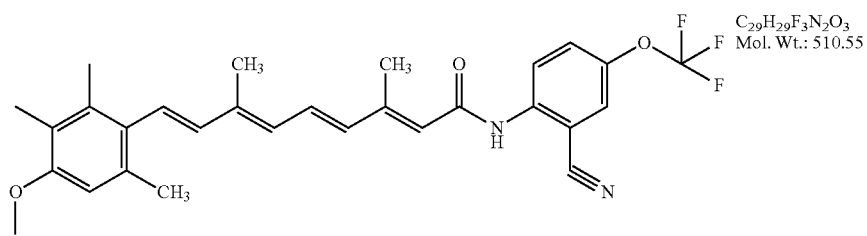

Formula (d-10) (2-cyano-4-trifluoromethoxyphenyl)-(all-trans)-9-(4-methoxy-2,3,6-trimethylphenyl)-3,7-dimethyl-2,4,6,8-nonatetraenoic acid amide

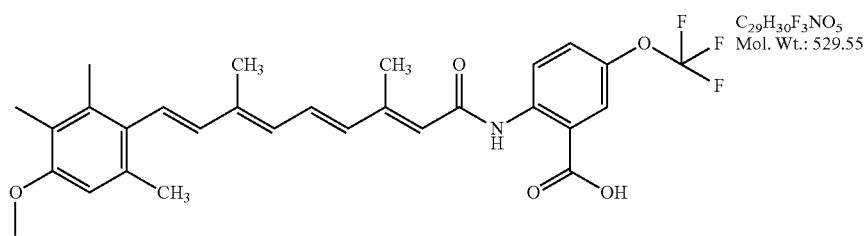

Formula (d-11) (2-carboxy-4-trifluoromethoxyphenyl)-(all-trans)-9-(4-methoxy-2,3,6-trimethylphenyl)-3,7-dimethyl-2,4,6,8-nonatetraenoic acid amide -continued

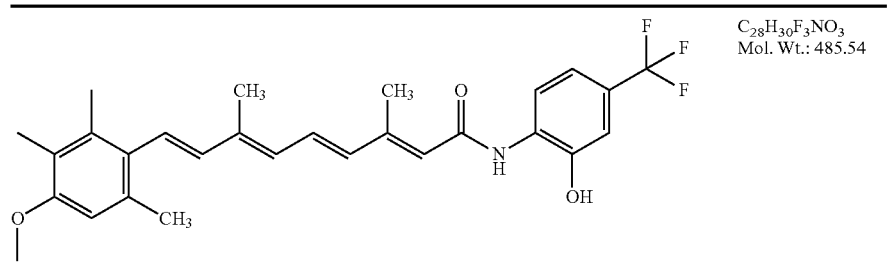

Formula (d-12) (2-hydroxy-4-trifluoromethylphenyl)-(all-trans)-9-(4-methoxy-2,3,6-trimethylphenyl)-3,7-dimethyl-2,4,6,8-nonatetraenoic acid amide

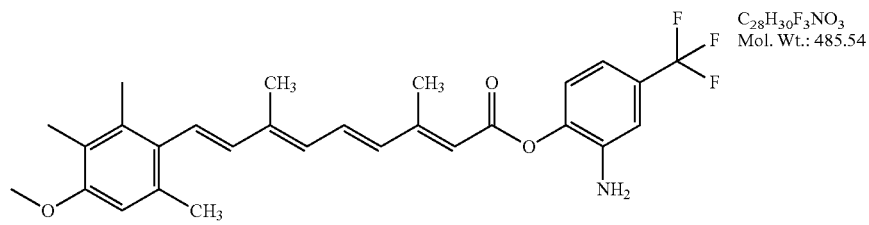

Formula (d-13) (2-amino-4-trifluoromethylphenyl)-(all-trans)-9-(4-methoxy-2,3,6-trimethylphenyl)-3,7-dimethyl-2,4,6,8-nonatetraenoate

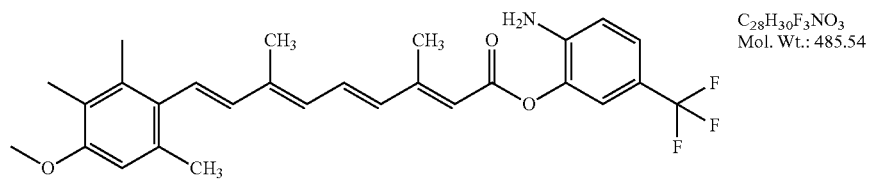

Formula (d-14) (2-amino-5-trifluoromethylphenyl)-(all-trans)-9-(4-methoxy-2,3,6-trimethylphenyl)-3,7-dimethyl-2,4,6,8-nonatetraenoate

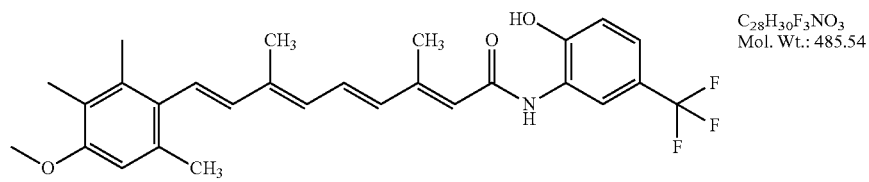

Formula (d-15) (2-hydroxy-5-trifluoromethylphenyl)-(all-trans)-9-(4-methoxy-2,3,6-trimethylphenyl)-3,7-dimethyl-2,4,6,8-nonatetraenoic acid amide The new retinoid derivatives above can be in their neutral forms, and, when they are alkali, they can be added with inorganic or organic acids to form the corresponding salts for use. The acids which can be used in the drugs include: hydrochloric acid, hydrogen bromide, naphthalene disulfonic acid (1, 5), phosphoric acid, nitric acid, sulfuric acid, oxalic acid, tartaric acid, lactic acid, salicylic acid, benzoic acid, formic acid, acetic acid, propionic acid, pentanoic acid, diethylacetic acid, malonic acid, succinic acid, fumaric acid, pimelic acid, hexanedioic acid, maleic acid, malic acid, sulfamic acid, phenpropionic acid, gluconic acid, ascorbic acid, isonicotinic acid, methanesulfonic acid, p-toluenesulfonic acid, citric acid and amino acid. The compounds can be added with multimolar acids to form salts. Such polymolar acids can be single or combined, which is mainly depended on the corresponding solvents and dilutions, and the added salts can be transformed into neutral forms by the anion exchange process, etc.

The invention further aims to provide a pharmaceutical composition including the therapeutically effective amount of retinoid derivative or an isomer, enantiomer, racemate, diastereomer mixture, racemic mixture, solvate, polymorph or pharmaceutically acceptable salt of the retinoid derivative as the active ingredient, and a pharmaceutically acceptable excipient. The pharmaceutically acceptable excipient includes the corresponding medically applicable excipients, adhesives, sustained release agents, stabilizing agents, spices, flavouring agents and pigments, and the dosage form is tablet, capsule, injection or lyophilized powder injection.

The invention further aims to provide the use of the compound. The retinoid derivative or an isomer, enantiomer, racemate, diastereomer mixture, racemic mixture, solvate, polymorph or pharmaceutically acceptable salt thereof is applied in the preparation of drugs which are capable of preventing or treating hematological tumours, such as acute leukemia, chronic leukemia, multiple myeloma and lymphoma, solid tumours, such as liver cancer, rectal cancer, mammary cancer and esophagus cancer, and skin disorders, such as psoriasis and acne.

| A: CONTROL | B: DMSO |
|---|---|
| C: Ethanol | D: Fenretinide (DMSO) |
| E: Fenretinide (Ethanol) | F: 6a-02 (DMSO) |
| G: 3a-01 (DMSO) | H: 6a-01 (DMSO) |
| I: 3a-01 (DMSO) | J: 2a-03 (Ethanol) |
| K: 4a-02 (DMSO) | |

Figure 2:
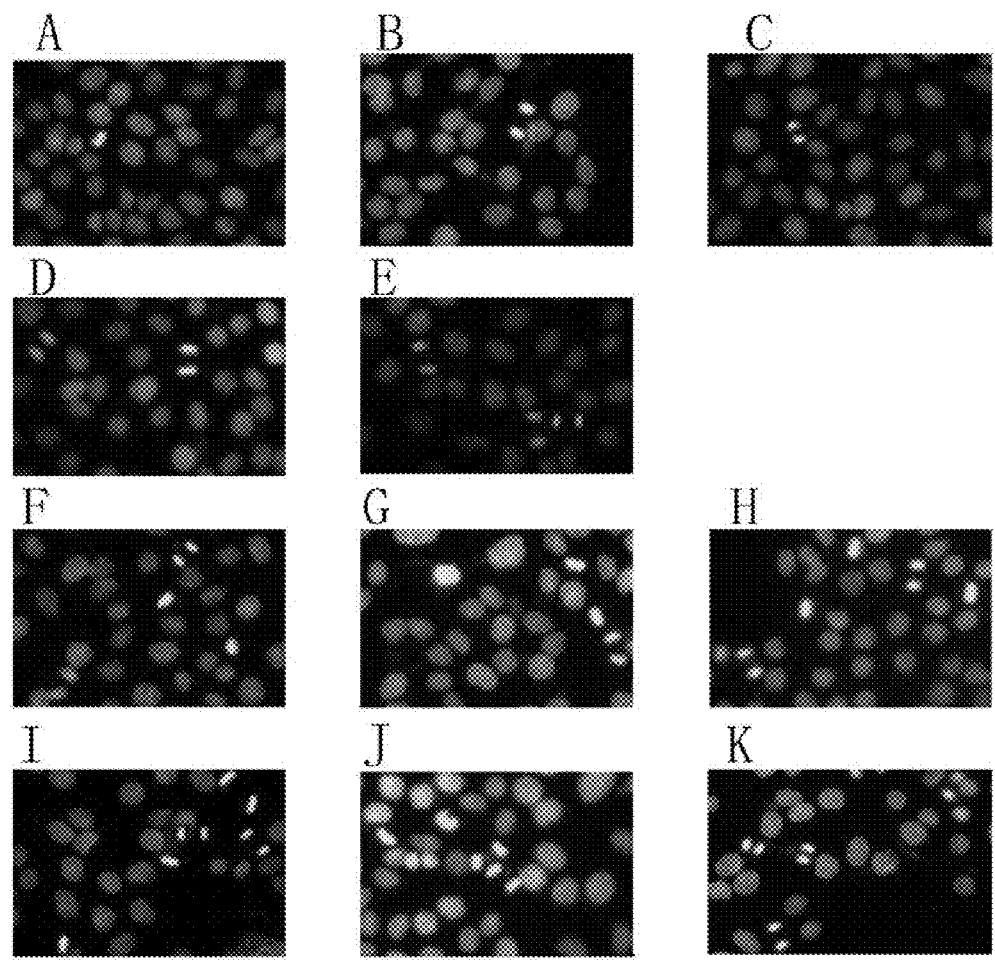

FIG. 2: HepG2 cell morphologic change (dosage of 10 ug/ml, 3 days)

| A: CONTROL | B: DMSO |
|---|---|
| C: Ethanol | D: Fenretinide (DMSO) |
| E: Fenretinide (Ethanol) | F: 6a-02 (DMSO) |
| G: 3a-01 (DMSO) | H: 6a-01 (DMSO) |
| I: 3a-01 (DMSO) | J: 2a-03 (Ethanol) |
| K: 4a-02 (DMSO) | |

Figure 3:
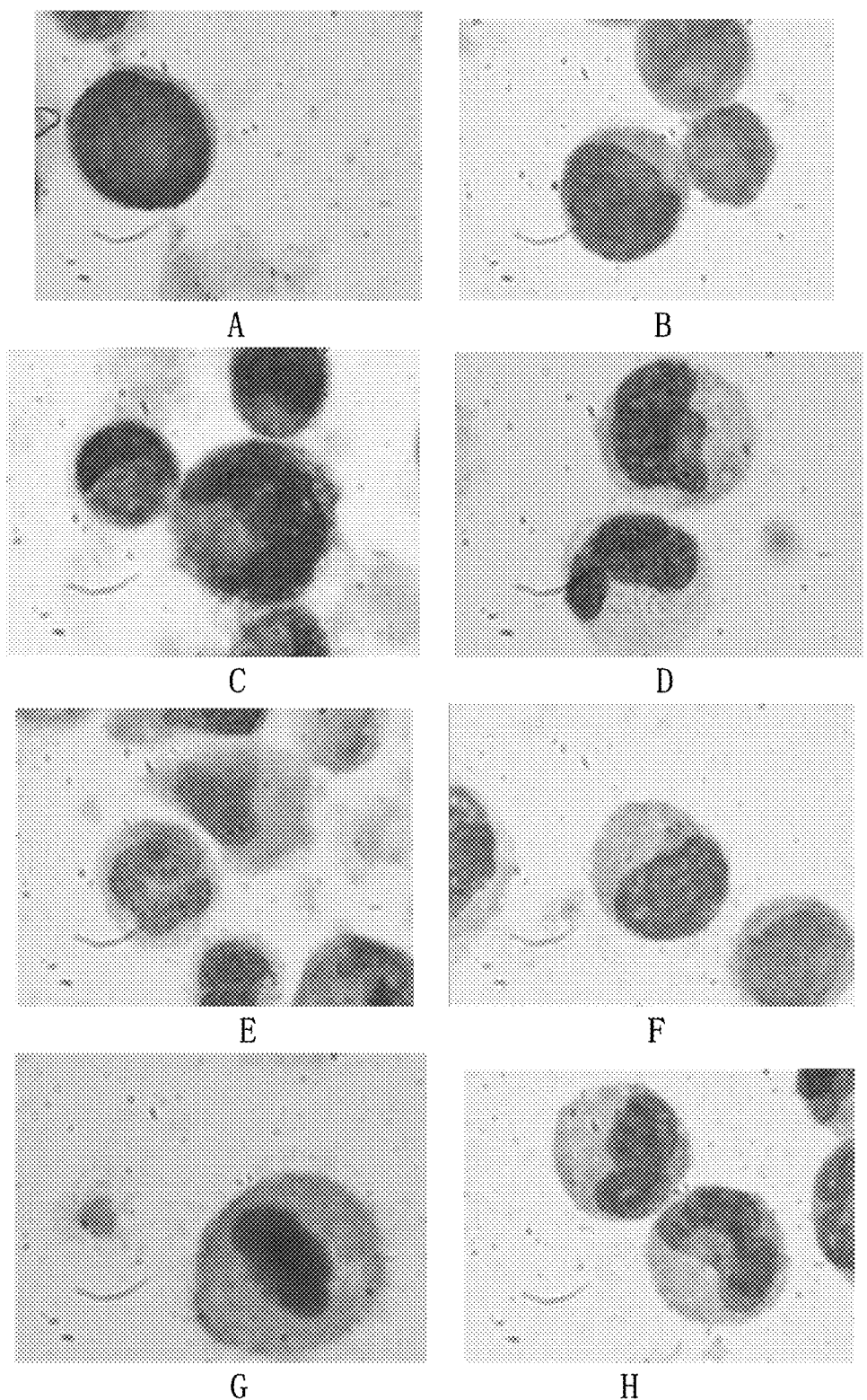

FIG. 3: NB4 cell morphologic change treated by the retinoic acid derivative, 72 h

| A, B: blank control group NB4 cell | C: 6a-02 5 (μg/ml) |
|---|---|
| D: 4a-02 5 (g/ml) | E: 4a-01 5 (g/ml) |
| F: 2a-03 5 (g/ml) | G: 3a-02 5 (g/ml) |
| H: Fenretinide 5 (μg/ml) | |

Figure 4:
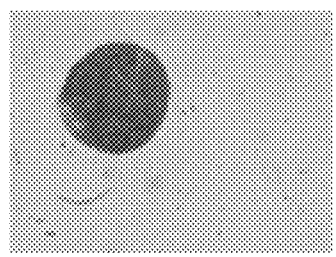
Figure 4:
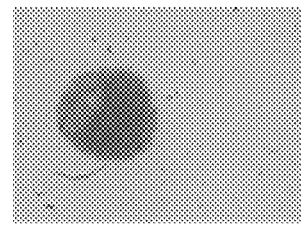
Figure 4:
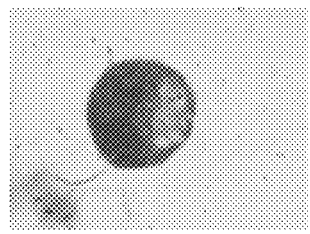
Figure 4:
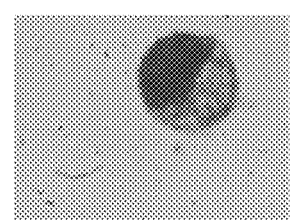
Figure 4:
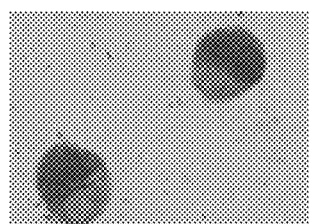
Figure 4:
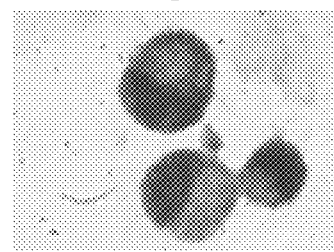
Figure 4:
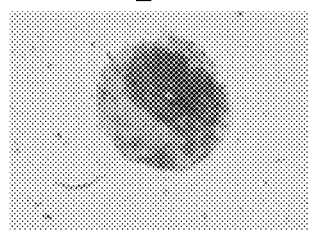
Figure 4:
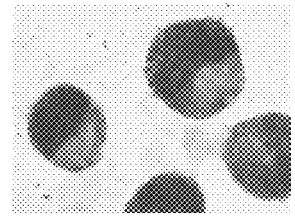
Figure 4:
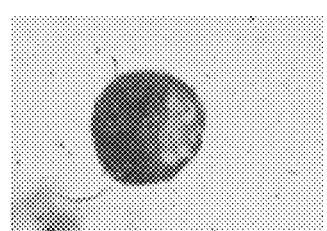
Figure 4:
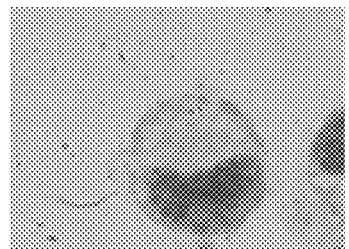

FIG. 4: K562 cell morphologic change treated by the retinoic acid derivative, 72 h

| , B: blank control group K562 cell | B: 6a-02 5 (μg/ml) |
|---|---|
| C: 6a-01 5 (μg/ml) | D: 4a-02 5 (μg/ml) |
| E: 5a-02 5 (μg/ml) | F: 4a-01 5 (μg/ml) |
| G: 2a-03 5 (μg/ml) | H: 3a-02 5 (μg/ml) |
| I: Fenretinide 5 (μg/ml) | J: 2a-01 5 (μg/ml) |

Figure 5:
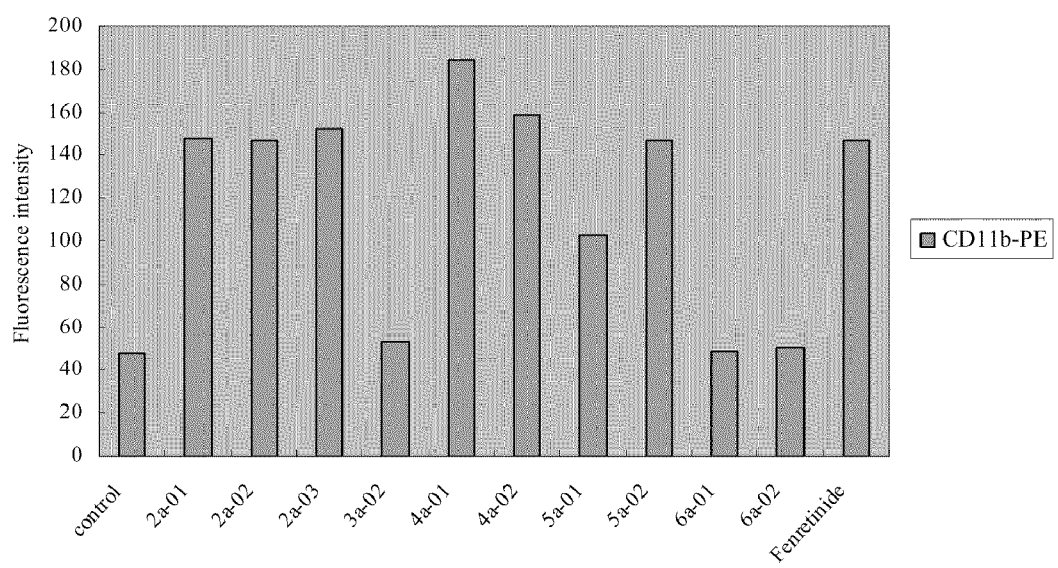

FIG. 5: Flow detection result bar chart of surface CD11b expression of each group of NB4 cells

DETAILED DESCRIPTION OF THE INVENTION

The following detailed examples are used for the preparation methods, but not limiting the contents disclosed. The used reagents and intermediates are commercially provided, or prepared by those skilled in the art of organic synthesis according to the methods of standard documents. Those skilled in the art also know other methods for preparing the compounds of the invention.

Example 1

(4-trifluoromethylphenyl)-(all-trans)-3,7-dimethyl-9-(2,6,6-trimethyl-1-cyclohexen-1-yl)-2,4,6,8-nonatetraenoate (2a-01)

At the room temperature, retinoic acid of 0.5 g and dichloromethane of 10 ml are added and stirred; 4-trifluoromethylphenol of 0.4 g, 4-dimethylaminopyridine (DMAP) of 0.23 g, N,N-dicyclohexylcarbodiimide (DCC) of 0.4 g and dichloromethane solution are added to obtain a yellow, transparent liquid which is stirred at the room temperature for 20 h; and saturated ammonium chloride solution is added to stop the reaction, followed by extraction by dichloromethane, washing by water, drying by anhydrous sodium sulphate, suction filtration, concentration, column chromatography (mobile phase: petroleum ether: 60-90° C.) and recrystallization by ethanol to obtain a yellow solid of 0.23 g. mp 118.5-120.4° C.

$^1$HNMR (CDCl$_3$), δ(ppm): 1.04 (s, 6H); 1.72 (s, 3H); 2.00 (s, 3H); 2.41 (s, 3H); 1.47+1.62 (t, 4H); 2.02 (m, 2H); 5.98 (s, 1H); 6.15-6.39 (m, 4H); 7.11 (m, 1H); 7.66 (d, 1H); 7.24 (s, 1H)

$^{13}$CNMR (CDCl$_3$), δ(ppm): 13.06; 14.26; 19.29; 21.83; 29.05; 33.22; 34.36; 39.71; 116.45; 129.37; 129.50; 130.41; 132.59; 134.55; 137.20; 137.76; 140.94; 156.71; 164.85; 122.35; 127.59; 153.51; 127.59-128.71 (q); 122.11-123.52 (q)

High-resolution MS: m/z: 444.2271 (theoretical value: 444.2276) molecular formula:

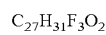

Example 2

(3-trifluoromethylphenyl)-(all-trans)-3,7-dimethyl-9-(2,6,6-trimethyl-1-cyclohexen-1-yl)-2,4,6,8-nonatetraenoate (2a-02)

The operating method is the same as Example 1, except for replacing p-trifluoromethylphenol with m-trifluoromethylphenol; column chromatography (mobile phase: petroleum ether: 60-90° C.) to obtain an oily matter of 0.21 g.

$^1$HNMR (CDCl$_3$), δ(ppm): 1.04 (s, 6H); 1.72 (s, 3H); 2.00 (s, 3H); 2.41 (s, 3H); 1.47+1.62 (t, 4H); 2.02 (m, 2H); 5.98 (s, 1H); 6.15-6.39 (m, 4H); 7.08 (m, 1H); 7.50 (m, 1H); 7.41 (s, 1H); 7.25 (m, 1H)

$^{13}$CNMR (CDCl$_3$), δ(ppm): 13.04; 14.24; 19.29; 21.82; 29.04; 33.22; 34.36; 39.70; 116.45; 129.38; 129.46; 130.18; 132.56; 134.57; 137.22; 137.75; 140.89; 156.65; 164.97; 119.18; 122.28; 125.51; 130.18; 131.74; 137.39; 151.03

High-resolution MS: m/z: 444.2278 (theoretical value: 444.2276) molecular formula:

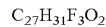

Example 3

(2-trifluoromethylphenyl)-(all-trans)-3,7-dimethyl-9-(2,6,6-trimethyl-1-cyclohexen-1-yl)-2,4,6,8-nonatetraenoate (2a-03)

The operating method is the same as Example 2, except for replacing p-trifluoromethylphenol with o-trifluoromethylphenol; column chromatography (mobile phase: petroleum ether: 60-90° C.) and recrystallization by ethanol to obtain an oily matter of 0.18 g, mp 93.8-95° C.

$^1$HNMR (CDCl$_3$), δ(ppm): 1.04 (s, 6H); 1.73 (s, 3H); 2.03 (s, 3H); 2.40 (s, 3H); 1.47+1.62 (t, 4H); 2.05 (m, 2H); 6.02 (s, 1H); 6.15-6.41 (m, 4H); 7.10 (m, 1H); 7.68 (d, 1H); 7.57 (t, 1H); 7.26-7.34 (m, 1H)

$^{13}$CNMR (CDCl$_3$), δ(ppm): 13.06; 14.24; 19.31; 21.84; 29.06; 33.23; 34.37; 39.72; 116.28; 129.40; 129.44; 130.37; 132.54; 134.66; 137.26; 137.77; 140.82; 156.75; 164.78; 148.52; 133.06; 130.22; 126.88; 125.57; 124.43

High-resolution MS: m/z: 444.2275 (theoretical value: 444.2276) molecular formula:

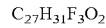

Example 4

(4-trifluoromethylphenyl)-(all-trans)-3,7-dimethyl-9-(2,6,6-trimethyl-1-cyclohexen-1-yl)-2,4,6,8-nonatetraenoic acid amide (3a-01)

In a reaction flask, retinoic acid of 0.5 g, toluene of 5 ml and phosphorus trichloride of 0.11 ml are added and stirred at the room temperature for 3 h, and the resultant solution is added in a solution of 4-(trifluoromethyl)aniline of 0.18 ml and pyridine of 5 ml, stirred to react with one another for 5 h in the cooling condition, and stirred at the room temperature overnight; the reaction liquid is poured in the crushed ice, followed by pH regulation to 1 by concentrated hydrochloric acid, extraction by ethyl acetate for three times, organic layer washing by saturated sodium chloride, drying by anhydrous sodium sulphate, filtration, reduced pressure concentration to dryness and recrystallization by ethanol to obtain a bright yellow product of 0.3 g, mp 186.1-187.6° C.

$^1$HNMR (CDCl$_3$), δ(ppm): 1.03 (s, 6H); 1.72 (s, 3H); 2.01 (s, 3H); 2.43 (s, 3H); 1.46+1.63 (t, 4H); 2.02 (m, 2H); 5.79 (s, 1H); 6.12-6.30 (m, 4H); 7.03 (m, 1H); 7.55 (d, 1H); 7.68 (d, 1H)

$^{13}$CNMR (CDCl$_3$), δ(ppm): 13.01; 13.90; 19.31; 21.82; 29.04; 33.21; 34.36; 39.71; 120.48; 128.98; 129.45; 130.18; 131.23; 134.98; 137.27; 137.80; 139.95; 152.13; 165.34; 119.26; 126.33; 141.50

High-resolution MS: m/z: 443.2444 (theoretical value: 443.2436) molecular formula:

$C_{27}H_{32}F_3NO$

Example 5

(3-trifluoromethylphenyl)-(all-trans)-3,7-dimethyl-9-(2,6,6-trimethyl-1-cyclohexen-1-yl)-2,4,6,8-nonatetraenoic acid amide (3a-02)

In a reaction flask, retinoic acid of 0.5 g, m-(trifluoromethyl)aniline of 0.32 g, 4-dimethylaminopyridine (DMAP) p-toluene sulphonate of 0.56 g and dichloromethane of 5 ml are added and stirred in the condition of ice bath with white insoluble substances generated; DDC of 0.4 g and dichloromethane solution are added with the reaction liquid changed into orange red and stirred at the room temperature overnight; and saturated ammonium chloride solution is added to stop the reaction, followed by extraction by dichloromethane, washing by water, drying by anhydrous sodium sulphate, concentration, column chromatography (petroleum ether: 60-90° C.), fraction collection, concentration and recrystallization by methanol to obtain a yellow solid of 200 mg, mp 89.7-92.5° C.

$^1$HNMR (CDCl$_3$), δ(ppm): 1.03 (s, 6H); 1.72 (s, 3H); 2.01 (s, 3H); 2.44 (s, 3H); 1.47+1.62 (t, 4H); 2.02 (m, 2H); 5.78 (s, 1H); 6.15-6.30 (m, 4H); 7.03 (m, 1H); 7.72 (d, 1H); 7.22 (s, 1H); 7.33, 7.45 (m, 1H); N—H 7.88 (s, 1H)

$^{13}$CNMR (CDCl$_3$), δ(ppm): 13.00; 13.88; 19.31; 21.82; 29.04; 33.21; 34.36; 39.71; 116.47; 129.49; 129.53; 130.15; 131.11; 135.06; 137.29; 137.81; 139.84; 151.92; 165.39; 138.95; 128.90; 125.33; 122.63 (d); 120.50; 131.29 (q)

High-resolution MS: m/z: 443.2437 (theoretical value: 443.2436) molecular formula:

$C_{27}H_{32}F_3NO$

Example 6

(4-amino-3-trifluoromethylphenyl)-(all-trans)-3,7-dimethyl-9-(2,6,6-trimethyl-1-cyclohexen-1-yl)-2,4,6,8-nonatetraenoate (4a-01)

At the room temperature, retinoic acid of 0.18 g, 4-amino-3-trifluoromethylphenol of 0.1 g, 4-dimethylaminopyridine (DMAP) of 0.09 g and dichloromethane of 10 ml are added and stirred; N,N-dicyclohexylcarbodiimide (DCC) of 0.15 g and dichloromethane solution are added to obtain a yellow, transparent liquid which is stirred at the room temperature for 20 h; and saturated ammonium chloride solution is added to stop the reaction, followed by extraction by dichloromethane, washing by water, drying by anhydrous sodium sulphate, suction filtration, concentration, column chromatography (mobile phase: petroleum ether: 60-90° C.: ethyl acetate=40:1), concentration and recrystallization by methanol to obtain a yellow solid of 0.09 g. mp 119.7-121.2° C.

$^1$HNMR (CDCl$_3$), δ(ppm): 0.96 (s, 6H); 1.65 (s, 3H); 1.95 (s, 3H); 2.32 (s, 3H); 1.40+1.56 (t, 4H); 1.97 (m, 2H); 5.88 (s, 1H); 6.07-6.30 (m, 4H); 7.00 (m, 1H); 7.12 (d); 7.01 (s); 6.65 (d); 4.03 (s, 2H) NH2

High-resolution MS: m/z: 459.2379 (theoretical value: 459.2385) molecular formula:

$C_{27}H_{32}F_3NO_2$

Example 7

(4-amino-2-trifluoromethylphenyl)-(all-trans)-3,7-dimethyl-9-(2,6,6-trimethyl-1-cyclohexen-1-yl)-2,4,6,8-nonatetraenoate (4a-02)

At the room temperature, retinoic acid of 0.5 g, 4-amino-2-trifluoromethylphenol of 0.32 g, 4-dimethylaminopyridine (DMAP) of 0.23 g and dichloromethane of 10 ml are added and stirred; N,N-dicyclohexylcarbodiimide (DCC) of 0.4 g and dichloromethane solution are added to obtain a yellow, transparent liquid which is stirred overnight; and saturated ammonium chloride solution is added to stop the reaction, followed by extraction by dichloromethane, washing by water, drying by anhydrous sodium sulphate, suction filtration, concentration, column chromatography (mobile phase: petroleum ether: 60-90° C.: ethyl acetate=2:1), concentration and recrystallization by petroleum ether (60-90° C.) to obtain a yellow solid of 0.21 g. mp 89.7-91.3° C.

$^1$HNMR (CDCl$_3$), δ(ppm): 1.04 (s, 6H); 1.72 (s, 3H); 2.02 (s, 3H); 2.39 (s, 3H); 1.46+1.63 (t, 4H); 2.03 (m, 2H); 5.99 (s, 1H); 6.14-6.39 (m, 4H); 7.08 (m, H); 7.02 (m); 6.91 (d, 1H); 6.82 (t, 1H)

$^{13}$CNMR (CDCl$_3$), δ(ppm): 13.03; 14.16; 19.30; 21.83; 29.05; 33.21; 34.36; 39.71; 118.63; 129.21; 129.48; 130.29; 130.20; 134.81; 137.28; 137.76; 140.52; 156.02; 165.55; 112.54; 112.58; 116.69; 125.45; 139.81; 144.12; 123.34

High-resolution MS: m/z: 459.2378 (theoretical value: 459.2385) molecular formula:

$C_{27}H_{32}F_3NO_2$

Example 8

(4-trifluoromethoxyphenyl)-(all-trans)-3,7-dimethyl-9-(2,6,6-trimethyl-1-cyclohexen-1-yl)-2,4,6,8-nonatetraenoate (5a-01)

At the room temperature, retinoic acid of 0.5 g, 4-trifluoromethylphenol of 0.4 g, 4-dimethylaminopyridine (DMAP)

of 0.23 g and dichloromethane of 10 ml are added and stirred; N,N-dicyclohexylcarbodiimide (DCC) of 0.4 g and dichloromethane solution are added to obtain a yellow and transparent liquid which is stirred at the room temperature for 20 h; and saturated ammonium chloride solution is added to stop the reaction, followed by extraction by dichloromethane, washing by water, drying by anhydrous sodium sulphate, suction filtration, concentration, column chromatography (mobile phase: petroleum ether: 60-90° C.), fraction collection, concentration and recrystallization by ethanol to obtain a yellow solid of 0.11 g. mp 88.3-90.6° C.

$^1$HNMR (CDCl$_3$), δ(ppm): 1.04 (s, 6H); 1.72 (s, 3H); 2.03 (s, 3H); 2.41 (s, 3H); 1.47+1.62 (t, 4H); 2.02 (m, 2H); 5.98 (s, 1H); 6.15-6.39 (m, 4H); 7.06 (m, 1H); 7.24 (d, 1H); 7.14 (d, 1H)

$^{13}$CNMR (CDCl$_3$), δ(ppm): 13.04; 14.21; 19.29; 21.82; 29.04; 33.21; 34.35; 39.70; 116.65; 129.40; 129.40; 130.37; 132.42; 134.62; 137.22; 137.75; 140.79; 156.36; 165.19; 149.18; 146.38; 123.17; 122.06; 122.90 (q)

High-resolution MS: m/z: 460.2219 (theoretical value: 460.2225) molecular formula:

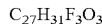

$C_{27}H_{31}F_3O_3$

Example 9

(3-trifluoromethoxyphenyl)-(all-trans)-3,7-dimethyl-9-(2,6,6-trimethyl-1-cyclohexen-1-yl)-2,4,6,8-nonatetraenoate (5a-02)

The operation is the same as Example 8; except for column chromatography (mobile phase: petroleum ether: 60-90° C.) to obtain an oily matter.

$^1$HNMR (CDCl$_3$), δ(ppm): 1.04 (s, 6H); 1.72 (s, 3H); 2.03 (s, 3H); 2.41 (s, 3H); 1.47+1.62 (t, 4H); 2.02 (m, 2H); 5.59 (s, 1H); 6.15-6.39 (m, 4H); 7.04 (m, 1H); 7.41 (t, 1H); 7.04-7.10 (m, 1H)

$^{13}$CNMR (CDCl$_3$), δ(ppm): 13.06; 14.25; 19.30; 21.83; 29.05; 33.23; 34.37; 39.71; 116.55; 129.40; 130.44; 130.39; 132.50; 134.61; 137.22; 137.77; 140.85; 156.55; 164.90; 151.66; 149.66; 130.20; 120.45; 117.83; 115.19; 116.89 (q)

High-resolution MS: m/z: 460.2221 (theoretical value: 460.2225) molecular formula:

$C_{27}H_{31}F_3O_3$

Example 10

(4-trifluoromethoxyphenyl)-(all-trans)-3,7-dimethyl-9-(2,6,6-trimethyl-1-cyclohexen-1-yl)-2,4,6,8-nonatetraenoic acid amide (6a-01)

In a reaction flask, retinoic acid of 0.5 g, p-(trifluoromethoxy)aniline of 0.35 g, 4-dimethylaminopyridine (DMAP) p-toluene sulphonate of 0.56 g and dichloromethane of 5 ml are added and stirred in the condition of ice bath with white insoluble substances generated; DDC of 0.4 g and dichloromethane solution are added with the reaction liquid changed into orange red and stirred at the room temperature overnight; and saturated ammonium chloride solution is added to stop the reaction, followed by extraction by dichloromethane, washing by water, drying by anhydrous sodium sulphate, concentration, column chromatography (petroleum ether: 60-90° C.), fraction collection, concentration, and recrystallization by methanol to obtain a yellow solid of 0.05 g, mp 89.7-174.5.5° C.

$^1$HNMR (CDCl$_3$), δ(ppm): 0.96 (s, 6H); 1.64 (s, 3H); 1.94 (s, 3H); 2.35 (s, 3H); 1.40+1.55 (t, 4H); 1.95 (m, 2H); 5.70 (s, 1H); 6.05-6.23 (m, 4H); 6.95 (m, 1H); 7.51 (d, 1H); 7.11 (d, 1H); N—H 7.09 (s, 1H)

$^{13}$CNMR (CDCl$_3$), δ(ppm): 13.01; 13.86; 19.32; 21.83; 29.05; 33.21; 34.37; 39.72; 121.83; 128.86; 129.50; 130.13; 130.97; 135.11; 137.32; 137.82; 139.74; 151.59; 165.14; 120.64; 120.86; 137.04

High-resolution MS: m/z: 459.2379 (theoretical value: 459.2385) molecular formula:

$C_{27}H_{32}F_3NO_2$

Example 11

(3-trifluoromethoxyphenyl)-(all-trans)-3,7-dimethyl-9-(2,6,6-trimethyl-1-cyclohexen-1-yl)-2,4,6,8-nonatetraenoic acid amide (6a-02)

The operation is the same as Example 10; except for column chromatography (petroleum ether: 60-90° C.), and recrystallization by methanol to obtain a yellow solid of 0.09 g, mp 139.2-140° C.

$^1$HNMR (CDCl$_3$), δ(ppm): 0.96 (s, 6H); 1.65 (s, 3H); 1.94 (s, 3H); 2.36 (s, 3H); 1.40+1.56 (t, 4H); 1.95 (m, 2H); 5.70 (s, 1H); 6.05-6.23 (m, 4H); 6.95 (m, 1H); 7.22-7.29 (m, 1H); 6.86-6.88 (m, 1H); N—H 7.10 (s, 1H)

$^{13}$CNMR (CDCl$_3$), δ(ppm): 13.04; 13.88; 19.32; 21.83; 29.05; 33.22; 34.37; 39.72; 120.53; 128.89; 129.50; 130.14; 130.09; 135.07; 137.31; 137.82; 139.83; 151.89; 165.15; 112.51; 116.13; 117.64; 119.08; 121.06; 130.02; 149.72

High-resolution MS: m/z: 459.2377 (theoretical value: 459.2385) molecular formula:

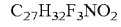

$C_{27}H_{32}F_3NO_2$

Example 12

(4-hydroxy-3-trifluoromethylphenyl)-(all-trans)-3,7-dimethyl-9-(2,6,6-trimethyl-1-cyclohexen-1-yl)-2,4,6,8-nonatetraenoic acid amide (7a-01)

In a reaction flask, retinoic acid of 0.5 g, toluene of 5 ml and phosphorus trichloride of 0.11 ml are added and stirred at the room temperature for 3 h, and the resultant solution is added in a solution of 4-hydroxy-3-trifluoromethylaniline of 0.17 g and pyridine of 5 ml, stirred to react with one another for 5 h in the cooling condition, and stirred at the room temperature overnight; and the reaction liquid is poured in the crushed ice, followed by pH regulation to 1 by concentrated hydrochloric acid, extraction by ethyl acetate for three times, organic layer washing by saturated sodium chloride, drying by anhydrous sodium sulphate, filtration, reduced pressure concentration to dryness, column chromatography (silica gel column: 100-200 meshes; mobile phase: petroleum ether: 60-90° C.:ethyl acetate=10:1), fraction collection, and concentration to obtain a yellow product of 0.08 g.

Example 13

(4-hydroxy-2-trifluoromethylphenyl)-(all-trans)-3,7-dimethyl-9-(2,6,6-trimethyl-1-cyclohexen-1-yl)-2,4,6,8-nonatetraenoic acid amide (7a-02)

The operation is the same as Example 12; except for column chromatography (silica gel column, 100-200 meshes;

mobile phase: petroleum ether: 60-90° C.:ethyl acetate=10:1), fraction collection, and concentration to obtain a yellow product of 0.12 g.

Example 14

(3-trifluoromethylphenyl)-(all-trans)-9-(4-methoxy-2,3,6-trimethylphenyl)-3,7-dimethyl-2,4,6,8-nonatetraenoate (2b-01)

In a reaction flask, etretin of 0.53 g, m-trifluoromethylphenol of 0.4 g, 4-dimethylaminopyridine (DMAP) of 0.4 g and dichloromethane of 5 ml are added and stirred in the condition of ice bath with white insoluble substances generated; DDC of 0.4 g and dichloromethane solution are added and stirred to react with one another for 4 h; and saturated ammonium chloride solution is added to stop the reaction, followed by extraction by dichloromethane, washing by saturated sodium chloride aqueous solution, drying by anhydrous sodium sulphate, concentration, and recrystallization by ethanol to obtain a yellow solid of 0.62 g, mp 121.5-123.1° C.

$^1$HNMR (CDCl$_3$), δ(ppm): 7.48 (d, 2H); 7.41 (s, 1H); 7.32 (m, 1H); 7.14 (dd, 1H); 6.76 (d, 1H); 6.71 (s, 1H); 6.42 (d, 1H); 6.29 (d, 1H); 6.22 (s, 1H); 6.00 (s, 1H); 3.82 (s, 3H); 2.43 (s, 3H); 2.3 (s, 3H); 2.24 (s, 5H); 2.15 (s, 3H); 2.13 (s, 3H)

$^{13}$CNMR (CDCl$_3$), δ(ppm): 164.72; 156.48; 156.37; 151.02; 140.47; 138.07; 136.02; 135.11; 134.02; 132.31; 132.09; 131.76; 130.18; 129.90; 129.80; 129.28; 125.50; 122.90; 122.35; 119.18; 116.78; 110.10; 55.60; 21.49; 17.54; 14.26; 13.11; 11.92

High-resolution MS: m/z: 470.2076 (theoretical value: 470.2069) molecular formula:

$C_{28}H_{29}F_3O_3$

Example 15

(2-trifluoromethylphenyl)-(all-trans)-9-(4-methoxy-2,3,6-trimethylphenyl)-3,7-dimethyl-2,4,6,8-nonatetraenoate (2b-2)

The operation is the same as Example 14, except for recrystallization by ethanol twice to obtain a yellow solid of 0.25 g, mp 117.7-121.2° C.

$^1$HNMR (CDCl$_3$), δ(ppm): 7.70 (d, 1H); 7.68 (OH); 7.36 (d, 1H); 7.32 (OH); 7.14 (q, 1H); 6.77 (d, 1H); 6.73 (s, 1H); 6.46 (d, 1H); 6.31 (d, 1H); 6.24 (s, 1H); 6.05 (s, 1H); 3.84 (s, 3H); 2.44 (s, 3H); 2.33 (s, 3H); 2.26 (s, 3H); 2.15 (s, 3H); 2.11 (s, 3H)

$^{13}$CNMR (CDCl$_3$), δ(ppm): 164.72; 156.57; 156.36; 148.49; 140.38; 138.11; 136.03; 135.18; 134.03; 132.88; 132.29; 130.23; 129.83; 129.20; 126.92; 126.88; 125.59; 124.70; 124.49; 123.36; 123.05; 122.88; 121.78; 116.60; 110.10; 55.61; 21.50; 17.54; 14.23; 13.11; 11.92

High-resolution MS: m/z: 470.2073 (theoretical value: 470.2069) molecular formula:

$C_{28}H_{29}F_3O_3$

Example 16

(4-trifluoromethylphenyl)-(all-trans)-9-(4-methoxy-2,3,6-trimethylphenyl)-3,7-dimethyl-2,4,6,8-nonatetraenoate (2b-03)

The operation is the same as Example 15, except for recrystallization by ethyl acetate to obtain a yellow solid of 570 mg, mp 162.5-164.7° C.

$^1$HNMR (CDCl$_3$), δ(ppm): 7.68 (d, 2H); 7.28 (t, 1H); 7.26 (s, 1H); 7.16 (q, 1H); 6.78 (d, 1H); 6.63 (s, 1H); 6.45 (d, 1H); 6.28 (t, 2H); 6.02 (s, 1H); 3.84 (s, 3H); 2.45 (s, 3H); 2.33 (s, 3H); 2.27 (s, 3H); 2.16 (s, 3H); 2.06 (s, 3H)

$^{13}$CNMR (CDCl$_3$), δ(ppm): 164.78; 156.53; 156.37; 153.49; 140.50; 138.05; 136.00; 135.07; 134.01; 132.34; 130.16; 129.78; 129.31; 126.73; 122.89; 122.33; 116.77; 110.09; 55.58; 21.48; 17.53; 14.25; 13.10; 11.91

High-resolution MS: m/z: 470.2065 (theoretical value: 470.2069) molecular formula:

$C_{28}H_{29}F_3O_3$

Example 17

(3-trifluoromethoxyphenyl)-(all-trans)-9-(4-methoxy-2,3,6-trimethylphenyl)-3,7-dimethyl-2,4,6,8-nonatetraenoic acid amide (3b-01)

In a reaction flask, etretin of 0.5 g, toluene of 10 ml and phosphorus trichloride of 0.19 ml are added and stirred at the room temperature for 2 h, and the resultant solution is added in a solution of m-trifluoromethylaniline of 0.25 g and pyridine of 6 ml in the cooling condition, and stirred to react with one another at the room temperature for 5 h; and the reaction liquid is poured in the crushed ice, followed by extraction by dichloromethane for three times, organic layer washing by saturated sodium bicarbonate, washing by water to neutrality, drying by anhydrous sodium sulphate, filtration, reduced pressure concentration to dryness, column chromatography (silica gel column: 100-200 meshes; mobile phase: petroleum ether: 60-90° C.:ethyl acetate=15:1), fraction collection, concentration, and recrystallization by methanol to obtain a yellow product of 0.1 g, mp 188.6-190.7° C.

$^1$HNMR (CDCl$_3$), δ(ppm): 7.88 (s, 1H); 7.74 (d, 1H); 7.43 (t, 1H); 7.35 (d, 1H); 7.25 (s, 1H); 7.06 (q, 1H); 6.72 (d, 1H); 6.60 (s, 1H); 6.33 (d, 1H); 6.22 (q, 2H); 5.79 (s, 1H); 3.82 (s, 3H); 2.45 (s, 3H); 2.30 (s, 3H); 2.24 (s, 3H); 2.15 (s, 3H); 2.10 (s, 3H)

$^{13}$CNMR (CDCl$_3$), δ(ppm): 165.22; 164.69; 156.31; 151.83; 149.87; 139.44; 138.90; 138.41; 138.17; 135.60; 132.13; 131.33; 130.91; 130.31; 129.93; 129.55; 128.73; 128.43; 122.87; 120.76; 118.90; 116.47; 110.14; 55.63; 21.49; 17.54; 13.89; 13.07; 11.91

High-resolution MS: m/z: 469.2234 (theoretical value: 469.2229) molecular formula:

$C_{28}H_{30}F_3NO_2$

Example 18

(2-trifluoromethoxyphenyl)-(all-trans)-9-(4-methoxy-2,3,6-trimethylphenyl)-3,7-dimethyl-2,4,6,8-nonatetraenoic acid amide (3b-00)

In a reaction flask, etretin of 0.5 g, toluene of 10 ml and phosphorus trichloride of 0.19 ml are added and stirred at the room temperature for 2 h, and the resultant solution is added in a solution of o-trifluoromethylaniline of 0.25 g and pyridine of 6 ml in the cooling condition, and stirred to react with one another at the room temperature for 5 h; and the reaction liquid is poured in the crushed ice, followed by extraction by dichloromethane for three times, organic layer washing by saturated sodium bicarbonate, washing by water to neutrality, drying by anhydrous sodium sulphate, filtration, reduced pressure concentration to dryness, column chromatography (silica gel column: 100-200 meshes; mobile phase: petroleum ether: 60-90° C.:ethyl acetate=20:1), fraction collection, concentration, and recrystallization by methanol to obtain a yellow product of 0.18 g, mp 165.5-166.5° C.

$^1$HNMR (CDCl$_3$), δ(ppm): 8.26 (d, 1H), 7.54 (d, 1H); 7.48 (t, 1H); 7.36 (s, 1H); 7.13 (t, 1H); 6.98 (q, 1H); 6.65 (d, 1H); 6.53 (s, 1H); 6.29 (d, 1H); 6.15 (q, 2H); 5.22 (s, 1H); 3.75 (s, 3H); 2.37 (s, 3H); 2.23 (s, 3H); 2.21 (s, 3H); 2.08 (s, 3H); 2.05 (s, 3H)

$^{13}$CNMR (CDCl$_3$), δ(ppm): 165.08; 156.31; 151.85; 139.39; 138.22; 135.65; 134.01; 132.85; 130.90; 130.36; 129.95; 128.70; 126.10; 124.10; 122.86; 120.92; 110.09; 55.63; 21.50; 17.55; 13.90; 13.07; 11.93

High-resolution MS: m/z: 469.2236 (theoretical value: 469.2229) molecular formula:

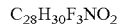

C$_{28}$H$_{30}$F$_3$NO$_2$

Example 19

(4-amino-3-trifluoromethylphenyl)-(all-trans)-9-(4-methoxy-2,3,6-trimethylphenyl)-3,7-dimethyl-2,4,6,8-nonatetraenoate (4b-01)

In a reaction flask, etretin of 0.53 g, 4-amino-3-trifluoromethylphenol of 0.28 g, 4-dimethylaminopyridine (DMAP) of 0.23 g and dichloromethane of 5 ml are added and stirred in the condition of ice bath with white insoluble substances generated; DDC of 0.4 g and dichloromethane solution are added and stirred to react with one another for 4 h; and saturated ammonium chloride solution is added to stop the reaction, followed by extraction by dichloromethane, washing by saturated sodium chloride aqueous solution, drying by anhydrous sodium sulphate, concentration, column chromatography (petroleum ether: 60-90° C.:ethyl acetate=20:1) and recrystallization by ethanol to obtain a yellow solid of 60 mg, mp 166.7-168.6° C.

$^1$HNMR (CDCl$_3$), δ(ppm): 7.22 (d, 1H); 7.12 (m, 1H); 7.09 (d, 1H); 6.79 (d, 1H); 6.72 (s, 1H); 6.62 (d, 1H); 6.43 (d, 1H); 6.30 (s, 1H); 6.26 (d, 1H); 5.98 (s, 1H); 3.84 (s, 3H); 2.43 (s, 3H); 2.32 (s, 3H); 2.26 (s, 3H); 2.14 (s, 3H); 2.11 (s, 3H)

$^{13}$CNMR (CDCl$_3$), δ(ppm): 13.04; 156.35; 155.84; 148.49; 140.21; 138.10; 136.03; 135.36; 134.94; 134.02; 132.01; 130.23; 129.83; 129.12; 126.68; 122.88; 120.00; 118.77; 117.13; 110.10; 55.61; 21.49; 17.53; 14.20; 13.10; 11.92

High-resolution MS: m/z: 485.2176 (theoretical value: 485.2178) molecular formula:

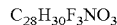

C$_{28}$H$_{30}$F$_3$NO$_3$

Example 20

(4-amino-2-trifluoromethylphenyl)-(all-trans)-9-(4-methoxy-2,3,6-trimethylphenyl)-3,7-dimethyl-2,4,6,8-nonatetraenoate (4b-02)

In a reaction flask, etretin of 0.53 g, 4-amino-2-trifluoromethylphenol of 0.28 g, 4-dimethylaminopyridine (DMAP) of 0.23 g and dichloromethane of 5 ml are added and stirred in the condition of ice bath with white insoluble substances generated; DDC of 0.4 g and dichloromethane solution are added and stirred to react with one another for 4 h; and saturated ammonium chloride solution is added to stop the reaction, followed by extraction by dichloromethane, washing by saturated sodium chloride aqueous solution, drying by anhydrous sodium sulphate, concentration, column chromatography (petroleum ether: 60-90° C.:ethyl acetate=20:1) and recrystallization by ethanol to obtain a yellow solid of 60 mg, mp 118.7-123.8° C.

$^1$HNMR (CDCl$_3$), δ(ppm): 7.39 (d, 1H); 7.26 (m, 1H); 7.12 (m, 1H); 6.75 (d, 1H); 6.61 (d, 1H); 6.43 (d, 1H); 6.30 (s, 1H); 6.26 (d, 1H); 6.01 (s, 1H); 3.82 (s, 3H); 2.42 (s, 3H); 2.31 (s, 3H); 2.25 (s, 3H); 2.14 (s, 3H); 2.09 (s, 3H)

$^{13}$CNMR (CDCl$_3$), δ(ppm): 165.62; 156.35; 155.93; 144.11; 140.15; 139.81; 138.14; 136.03; 135.33; 134.03; 132.02; 130.28; 129.88; 129.06; 125.43; 122.88; 121.07; 118.67; 116.98; 112.05; 110.10; 55.63; 21.49; 17.54; 14.19; 13.09; 11.92

High-resolution MS: m/z: 485.2177 (theoretical value: 485.2178) molecular formula:

C$_{28}$H$_{30}$F$_3$NO$_3$

Example 21

(4-trifluoromethoxyphenyl)-(all-trans)-9-(4-methoxy-2,3,6-trimethylphenyl)-3,7-dimethyl-2,4,6,8-nonatetraenoate (5b-01)

In a reaction flask, etretin of 0.53 g, p-trifluoromethoxyphenol of 0.4 g, 4-dimethylaminopyridine (DMAP) of 0.4 g and dichloromethane of 5 ml are added and stirred in the condition of ice bath with white insoluble substances generated; DDC of 0.4 g and dichloromethane solution are added and stirred to react with one another for 4 h; and saturated ammonium chloride solution is added to stop the reaction, followed by extraction by dichloromethane, washing by saturated sodium chloride aqueous solution, drying by anhydrous sodium sulphate, concentration, and recrystallization by ethanol to obtain a yellow solid of 0.67 g, mp 145.0-147.9° C.

$^1$HNMR (CDCl$_3$), δ(ppm): 7.26 (s, 1H); 7.24 (s, 1H); 7.19-7.11 (m, 3H); 6.77 (d, 1H); 6.63 (s, 1H); 6.40 (d, 1H); 6.27 (t, 2H); 6.01 (s, 1H); 3.84 (s, 3H); 2.44 (s, 3H); 2.33 (s, 3H); 2.26 (s, 3H); 2.17 (s, 3H); 2.15 (s, 3H)

$^{13}$CNMR (CDCl$_3$), δ(ppm): 13.06; 156.37; 156.17; 149.17; 146.40; 140.36; 138.07; 136.01; 135.15; 134.01; 132.17; 130.19; 129.80; 129.23; 123.16; 122.89; 122.06; 116.97; 110.10; 55.59; 21.48; 17.53; 14.21; 13.09; 11.91

High-resolution MS: m/z: 486.2015 (theoretical value: 486.2018) molecular formula:

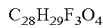

C$_{28}$H$_{29}$F$_3$O$_4$

Example 22

(3-trifluoromethoxyphenyl)-(all-trans)-9-(4-methoxy-2,3,6-trimethylphenyl)-3,7-dimethyl-2,4,6,8-nonatetraenoate (5b-02)

The operation is the same as Example 21, except for column chromatography (petroleum ether: 60-90° C.:ethyl acetate=100:1) and recrystallization by ethanol/ethyl acetate to obtain a yellow solid of 330 mg, mp 125.6-126.7° C.

$^1$HNMR (CDCl$_3$), δ(ppm): 7.43 (t, 1H); 7.24 (s, 1H); 7.10-7.06 (m, 3H); 6.78 (d, 1H); 6.63 (s, 1H); 6.44 (d, 1H); 6.31 (t, 2H); 6.00 (s, 1H); 3.84 (s, 3H); 2.45 (s, 3H); 2.33 (s, 3H); 2.26 (s, 3H); 2.17 (s, 3H); 2.15 (s, 3H)

$^{13}$CNMR (CDCl$_3$), δ(ppm): 13.06; 156.37; 151.65; 149.66; 140.42; 138.09; 136.03; 135.14; 134.03; 132.25; 130.19; 130.37; 129.25; 122.91; 120.44; 117.85; 116.88; 115.19; 110.11; 55.62; 21.50; 129.82; 14.26; 13.12; 11.93

High-resolution MS: m/z: 486.2014 (theoretical value: 486.2018) molecular formula:

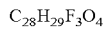

$C_{28}H_{29}F_3O_4$

Example 23

(3-trifluoromethoxyphenyl)-(all-trans)-9-(4-methoxy-2,3,6-trimethylphenyl)-3,7-dimethyl-2,4,6,8-nonatetraenoic acid amide (6b-01)

In a reaction flask, etretin of 0.5 g, toluene of 10 ml and phosphorus trichloride of 0.19 ml are added and stirred at the room temperature for 2 h, and the resultant solution is added in a solution of m-trifluoromethoxyaniline of 0.27 g and pyridine of 6 ml in the cooling condition, and stirred to react with one another at the room temperature for 5 h; and the reaction liquid is poured in the crushed ice, followed by extraction by dichloromethane for three times, organic layer washing by saturated sodium bicarbonate, washing by water to neutrality, drying by anhydrous sodium sulphate, filtration, reduced pressure concentration to dryness, column chromatography (silica gel column: 100-200 meshes; mobile phase: petroleum ether: 60-90° C.:ethyl acetate=20:1), fraction collection, concentration, and recrystallization by methanol to obtain a yellow product of 0.20 g.

$^1$HNMR (CDCl$_3$), δ(ppm): 7.64 (s, 1H); 7.38 (d, 1H); 7.31 (t, 1H); 7.21 (s, 1H); 7.06 (q, 1H); 6.97 (d, 1H); 6.73 (d, 1H); 6.62 (s, 1H); 6.34 (d, 1H); 6.23 (q, 2H); 5.80 (s, 1H); 3.83 (s, 3H); 2.46 (s, 3H); 2.32 (s, 3H); 2.25 (s, 3H); 2.17 (s, 3H); 2.13 (s, 3H)

Example 24

(2-trifluoromethoxyphenyl)-(all-trans)-9-(4-methoxy-2,3,6-trimethylphenyl)-3,7-dimethyl-2,4,6,8-nonatetraenoic acid amide (6b-02)

The operation is the same as Example 23.

Example 25

(4-trifluoromethoxyphenyl)-(all-trans)-9-(4-methoxy-2,3,6-trimethylphenyl)-3,7-dimethyl-2,4,6,8-nonatetraenoic acid amide (6b-03)

The operation is the same as Example 23.

Example 26

(4-hydroxy-3-trifluoromethoxyphenyl)-(all-trans)-9-(4-methoxy-2,3,6-trimethylphenyl)-3,7-dimethyl-2,4,6,8-nonatetraenoic acid amide (7b-01)

In a reaction flask, etretin of 0.5 g, toluene of 10 ml and phosphorus trichloride of 0.19 ml are added and stirred at the room temperature for 2 h, and the resultant solution is added in a solution of 4-hydroxy-3-trifluoromethylphenylamine of 0.27 g and pyridine of 6 ml in the cooling condition, and stirred to react with one another for at the room temperature for 5 h; and the reaction liquid is poured in the crushed ice, followed by extraction by dichloromethane for three times, organic layer washing by saturated sodium bicarbonate, washing by water to neutrality, drying by anhydrous sodium sulphate, filtration, reduced pressure concentration to dryness, column chromatography (silica gel column: 100-200 meshes; mobile phase: petroleum ether: 60-90° C.:ethyl acetate=5:1), fraction collection, concentration, and recrystallization by methanol to obtain a yellow product of 0.20 g.

Example 27

(4-hydroxy-2-trifluoromethylphenyl)-(all-trans)-9-(4-methoxy-2,3,6-trimethylphenyl)-3,7-dimethyl-2,4,6,8-nonatetraenoic acid amide (7b-02)

The operation is the same as Example 26.

Example 28

Determination of bioactivities of retinoid derivatives to A549 lung cancer cells and HepG2

1 Materials and Method 1.1 Reagents 12 retinoic acid derivatives with the final concentrations of 1 ug/ml, 5 ug/ml and 10 ug/ml are synthesized by the Pharmaceutical College of Anhui Medical University using DMSO and anhydrous ethanol, separately packaged for storage at −20° C. and kept out of the light when used, and the final concentration of DMSO is less than 0.1%. MTT is purchased from Sigma Corp. The Coulter DNA detection kit is presented by the Central Lab of Anhui Provincial Hospital. AFP and γ-GT are provided by the Clinical Lab of No. 105 Hospital of PLA. Apoptosis-Hoechst staining kit is purchased from Beyotime Company.

1.2 Cell Culture A549, and HpeG2 cells are stored by our lab. Cell growth condition: DMEM (from GIBICO Company) culture solution is added with 10% of calf serum (purchased from the Hangzhou Sijiqing Biological Engineering Material Co., Ltd.) to culture in a cell culture incubator (37° C., 5% CO$_2$) with saturated humidity.

1.3 Cell Growth and Proliferation Experiments MTT process is used. Cells in the logarithmic phase are picked and seeded on a 96-hole culture board with a cell concentration of 5×10$^7$/L. Each hole of the board is 200 ul. The next day after the adherence, the original solution is discarded, and the culture solution is added. The cells are divided into 1 ug/ml retinoic acid derivative groups, 5 ug/ml retinoic acid derivative groups, 10 ug/ml retinoic acid derivative groups, blank control groups, cell control groups, solvent control groups (1‰ DMSO and anhydrous ethanol) (17 in total) according to the concentrations thereof, incubated for 3d, added with MTT (5 g/L) of 20 ul/hole for incubation at 37° C. for 4 h. The original solution is carefully discarded and dried, and DMSO of 20 ul/hole is added to dissolve crystals, followed by vibrating for 10 min and determining the OD value at 570 nm. Each concentration is corresponding to 5 holes, and each group calculates the average of 3 experiments to calculate the inhibition rate to the cell growth according to the optical density (OD) average of each hole in each group and the following equation: inhibition rate %=(control hole OD$_{570}$−experimental hole OD$_{570}$)/control hole OD$_{5700}$*100%. The process above is repeated for three times. The second experiment takes the maximum concentration (10 umol/L) for culture respectively for 1, 2, 3 and 7 days and repeat for three times.

1.4 Detection of Cell Cycle and Apoptosis by Flow Cytometry A549 cells in the logarithmic phase are collected, regulated with the concentrations thereof to 8×10$^7$/L, inoculated in a 6-hole board, cultured in an incubator (37° C. and 5% CO$_2$). After the cells are adhered, the culture solution is discarded, and a culture solution having drugs with the corresponding concentrations is added and divided into 10 μg/ml drug groups, 10 μg/ml fenretinide groups, cell control groups, solvent control groups (1‰ DMSO and anhydrous ethanol)

(11 in total). After 3 days, each group of cells is normally digested, collected, blown into single cell suspension, washed by cold PBS twice, and re-suspend by 10 μl PBS. Fixing and member breaking agents and a PI staining solution are added according to the Coulter DNA detection kit and reacted with one another at the room temperature and out of light for 30 min for machine detection. Each sample detects 10000 cells and repeats for three times, and the data are analyzed by Analysis software for the ratio during the $G_0$-$G_1$, S and $G_2$-M periods and the ratio of apoptotic cells.

1.5 Observation of A549 and HepG2 Cellular Morphology Fenretinide of 10 μg/ml acts on the cells in a cell bottle for 3d, then, observed and shot the changes of cellular morphology by an optical microscope, and divided into 10 μg/ml fenretinide control groups, cell control groups and solvent control groups.

1.6 Detection of Differentiation Index The cultured A549 cells are randomly divided into 6 10 μg/ml drug groups, cell control groups, solvent control groups (DMSO and ethanol) and 10 μg/ml fenretinide control groups (11 in total). The control groups and drug groups are cultured for 3 days to collect respective 3 tubes of cell culture solutions which are centrifugated at a speed of 4000 r/min for 5 min to take the supernatant and detect the CEA content of the kit by using enzyme kinetics and CEA detection.

2 Results 2.1 Effects of 1 ug/ml, 5 ug/ml and 10 ug/ml on the Proliferation of A549 See Table 1

TABLE 1

Effects on the proliferation of A549

| Group | Concentration | OD Value ($\bar{x} \pm s$) | Inhibition Rate |
|---|---|---|---|
| 6a-02 (D) | 1 ug/ml | 1.614 ± 0.146 | 0.135 |
|  | 5 ug/ml | 1.580 ± 0.096 | 0.154 |
|  | 10 ug/ml | 1.498 ± 0.218 | 0.197 |
| 3a-02 (D) | 1 ug/ml | 1.517 ± 0.100 | 0.187 |
|  | 5 ug/ml | 1.357 ± 0.159 | 0.273 |
|  | 10 ug/ml | 1.296 ± 0.192 | 0.305 |
| 6a-02 (D) | 1 ug/ml | 1.637 ± 0.146 | 0.123 |
|  | 5 ug/ml | 1.613 ± 0.120 | 0.136 |
|  | 10 ug/ml | 1.362 ± 0.077 | 0.270 |
| 3a-02 (D) | 1 ug/ml | 1.551 ± 0.083 | 0.169 |
|  | 5 ug/ml | 1.510 ± 0.193 | 0.191 |
|  | 10 ug/ml | 0.939 ± 0.040 | 0.497 |
| 2a-02 (D) | 1 ug/ml | 1.735 ± 0.048 | 0.070 |
|  | 5 ug/ml | 1.621 ± 0.070 | 0.131 |
|  | 10 ug/ml | 1.580 ± 0.207 | 0.144 |
| 5a-02 (D) | 1 ug/ml | 1.843 ± 0.179 | 0.012 |
|  | 5 ug/ml | 1.817 ± 0.142 | 0.027 |
|  | 10 ug/ml | 1.689 ± 0.154 | 0.095 |
| 2a-01 (Ethanol) | 1 ug/ml | 1.878 ± 0.158 | −0.006 |
|  | 5 ug/ml | 1.487 ± 0.175 | 0.203 |
|  | 10 ug/ml | 1.458 ± 0.066 | 0.219 |
| 2a-03 (Ethanol) | 1 ug/ml | 1.639 ± 0.115 | 0.122 |
|  | 5 ug/ml | 1.555 ± 0.162 | 0.167 |
|  | 10 ug/ml | 1.382 ± 0.133 | 0.260 |
| 5a-1 (Ethanol) | 1 ug/ml | 1.962 ± 0.225 | −0.051 |
|  | 5 ug/ml | 1.754 ± 0.138 | 0.060 |
|  | 10 ug/ml | 1.732 ± 0.317 | 0.072 |
| 4a-02 (D) | 1 ug/ml | 1.644 ± 0.272 | 0.119 |
|  | 5 ug/ml | 1.618 ± 0.087 | 0.133 |
|  | 10 ug/ml | 1.026 ± 0.0.069 | 0.450 |
| 4a-02 (D) | 1 ug/ml | 2.020 ± 0.317 | −0.083 |
|  | 5 ug/ml | 1.979 ± 0.138 | −0.060 |
|  | 10 ug/ml | 1.808 ± 0.143 | 0.031 |
| Control Group |  | 1.866 ± 0.073 |  |
| DMSO |  | 1.830 ± 0.099 | 0.019 |
| Ethanol |  | 1.805 ± 0.086 | 0.033 |
| Fenretinide (DMSO) |  | 1.724 ± 0.080 | 0.076 |
| Fenretinide (Ethanol) |  | 1.710 ± 0.056 | 0.083 |

Seen from the table above, each derivative has the inhibition effect in different degree to lung cancer cells.

Subsequently, 6 of them with obvious effect are selected for 3-time repeated MTT with the concentration of 10 ug/ml according to time gradient, see Table 2.

TABLE 2

Effects on the Proliferation of A549

| Group | Time | OD Value ($\bar{x} \pm s$) | Inhibition Rate |
|---|---|---|---|
| 6a-02 (1) (10 ug/ml) | 1 d | 0.774 ± 0.030 | 0.156 |
|  | 2 d | 1.065 ± 0.045 | 0.272 |
|  | 3 d | 0.408 ± 0.028 | 0.561 |
|  | 7 d | 0.666 ± 0.049 | 0.679 |
| 3a-01 (2) (10 ug/ml) | 1 d | 0.680 ± 0.055 | 0.258 |
|  | 2 d | 1.042 ± 0.046 | 0.288 |
|  | 3 d | 0.623 ± 0.006 | 0.328 |
|  | 7 d | 1.325 ± 0.028 | 0.361 |
| 6a-01 (3) (10 ug/ml) | 1 d | 0.646 ± 0.019 | 0.296 |
|  | 2 d | 0.909 ± 0.065 | 0.378 |
|  | 3 d | 0.567 ± 0.057 | 0.389 |
|  | 7 d | 1.243 ± 0.024 | 0.401 |
| 3a-02 (4) (10 ug/ml) | 1 d | 0.617 ± 0.072 | 0.327 |
|  | 2 d | 0.703 ± 0.025 | 0.519 |
|  | 3 d | 0.229 ± 0.010 | 0.753 |
|  | 7 d | 0.106 ± 0.035 | 0.949 |
| 2a-03 (8) (10 ug/ml) | 1 d | 0.902 ± 0.055 | 0.016 |
|  | 2 d | 1.066 ± 0.015 | 0.271 |
|  | 3 d | 0.635 ± 0.033 | 0.315 |
|  | 7 d | 1.393 ± 0.043 | 0.328 |
| 4a-02 (11) (10 ug/ml) | 1 d | 0.815 ± 0.045 | 0.111 |
|  | 2 d | 1.176 ± 0.021 | 0.196 |
|  | 3 d | 0.720 ± 0.025 | 0.223 |
|  | 7 d | 1.144 ± 0.150 | 0.448 |
| CELL | 1 d | 0.917 ± 0.048 | 0.000 |
|  | 2 d | 1.463 ± 0.086 | 0.000 |
|  | 3 d | 0.927 ± 0.045 | 0.000 |
|  | 7 d | 2.074 ± 0.053 | 0.000 |
| DMSO | 1 d | 0.913 ± 0.039 | 0.004 |
|  | 2 d | 1.289 ± 0.088 | 0.119 |
|  | 3 d | 0.832 ± 0.049 | 0.102 |
|  | 7 d | 1.821 ± 0.144 | 0.122 |
| Ethanol | 1 d | 0.902 ± 0.037 | 0.017 |
|  | 2 d | 1.442 ± 0.030 | 0.014 |
|  | 3 d | 0.916 ± 0.027 | 0.012 |
|  | 7 d | 2.041 ± 0.115 | 0.016 |
| Fenretinide (DMSO) | 1 d | 0.883 ± 0.062 | 0.037 |
|  | 2 d | 1.360 ± 0.052 | 0.070 |
|  | 3 d | 0.845 ± 0.034 | 0.089 |
|  | 7 d | 1.835 ± 0.030 | 0.115 |
| Fenretinide (Ethanol) | 1 d | 0.887 ± 0.057 | 0.033 |
|  | 2 d | 1.333 ± 0.046 | 0.089 |
|  | 3 d | 0.836 ± 0.034 | 0.099 |
|  | 7 d | 1.851 ± 0.030 | 0.108 |

It can be seen that the 6 drugs have better inhibition effect to lung cancer cells.

2.2 Effects of 1 ug/ml, 5 ug/ml and 10 ug/ml on the Proliferation of HepG2 See Table 3

TABLE 3

Effects on the Proliferation of HepG2

| Group | Concentration | OD Value ($\bar{x} \pm s$) | Inhibition Rate |
|---|---|---|---|
| 6a-02 | 1 ml | 1.38 ± 0.62 | 0.18 |
|  | 5/ml | 1.16 ± 0.38 | 0.31 |
|  | 10/ml | 0.84 ± 0.31 | 0.50 |
| 3a-01 | 1 ug/ml | 1.13 ± 0.16 | 0.33 |
|  | 5 ug/ml | 1.13 ± 0.45 | 0.33 |
|  | 10 ug/ml | 0.86 ± 0.13 | 0.49 |
| 6a-01 | 1 ug/ml | 0.97 ± 0.29 | 0.42 |
|  | 5 ug/ml | 0.89 ± 0.14 | 0.47 |
|  | 10 ug/ml | 0.89 ± 0.30 | 0.47 |

TABLE 3-continued

Effects on the Proliferation of HepG2

| Group | Concentration | OD Value ($\bar{x} \pm s$) | Inhibition Rate |
|---|---|---|---|
| 3a-02 | 1 ug/ml | 1.19 ± 0.50 | 0.30 |
|  | 5 ug/ml | 0.92 ± 0.27 | 0.45 |
|  | 10 ug/ml | 0.94 ± 0.41 | 0.45 |
| 2a-02 (Ethanol) | 1 ug/ml | 1.19 ± 0.52 | 0.29 |
|  | 5 ug/ml | 1.13 ± 0.46 | 0.33 |
|  | 10 ug/ml | 0.94 ± 0.49 | 0.45 |
| 5a-02 (Ethanol) | 1 ug/ml | 1.27 ± 0.44 | 0.25 |
|  | 5 ug/ml | 1.13 ± 0.47 | 0.33 |
|  | 10 ug/ml | 1.11 ± 0.61 | 0.35 |
| 2a-1 (Ethanol) | 1 ug/ml | 1.38 ± 0.56 | 0.18 |
|  | 5 ug/ml | 1.31 ± 0.57 | 0.23 |
|  | 10 ug/ml | 1.30 ± 0.55 | 0.24 |
| 2a-03 | 1 ug/ml | 1.32 ± 0.50 | 0.22 |
|  | 5 ug/ml | 1.32 ± 0.56 | 0.23 |
|  | 10 ug/ml | 0.98 ± 0.19 | 0.42 |
| 5a-1 (Ethanol) | 1 ug/ml | 1.57 ± 0.39 | 0.07 |
|  | 5 ug/ml | 1.51 ± 0.30 | 0.11 |
|  | 10 ug/ml | 1.49 ± 0.23 | 0.12 |
| 4a-02 | 1 ug/ml | 1.50 ± 0.24 | 0.11 |
|  | 5 ug/ml | 1.32 ± 0.50 | 0.22 |
|  | 10 ug/ml | 0.86 ± 0.13 | 0.49 |
| 4a-01 | 1 ug/ml | 1.72 ± 0.44 | −0.009 |
|  | 5 ug/ml | 1.63 ± 0.36 | 0.04 |
|  | 10 ug/ml | 1.57 ± 0.30 | 0.07 |
| Control Group |  | 1.70 ± 0.51 |  |
| DMSO |  | 1.45 ± 0.42 | 0.14 |
| Ethanol |  | 1.56 ± 0.40 | 0.08 |
| Fenretinide (DMSO) |  | 1.27 ± 0.25 | 0.25 |
| Fenretinide (Ethanol) |  | 1.28 ± 0.21 | 0.24 |

Seen from the table above, each derivative has the inhibition effect in different degree to liver cancer cells.

Subsequently, 6 of them with obvious effect are selected for 3-time repeated MTT with the concentration of 10 ug/ml according to time gradient, see Table 4.

TABLE 4

Effects on the proliferation of HepG2

| Group | Time | OD Value ($\bar{x} \pm s$) | Inhibition Rate |
|---|---|---|---|
| 6a-02 (1)* | 1 d | 1.60 ± 0.19 | 0.07 |
| (10 ug/ml) | 2 d | 1.14 ± 0.09 | 0.32 |
|  | 3 d | 0.81 ± 0.12 | 0.34 |
|  | 7 d | 0.49 ± 0.32 | 0.63 |
| 3a-01 (2) | 1 d | 1.52 ± 0.13 | 0.12 |
| (10 ug/ml) | 2 d | 0.71 ± 0.02 | 0.42 |
|  | 3 d | 0.77 ± 0.03 | 0.54 |
|  | 7 d | 0.30 ± 0.08 | 0.77 |
| 6a-01 (3) | 1 d | 1.28 ± 0.07 | 0.06 |
| (10 ug/ml) | 2 d | 1.55 ± 0.11 | 0.10 |
|  | 3 d | 1.24 ± 0.18 | 0.26 |
|  | 7 d | 0.62 ± 0.13 | 0.50 |
| 3a-02 (4)* | 1 d | 1.43 ± 0.07 | 0.17 |
| (10 ug/ml) | 2 d | 0.81 ± 0.12 | 0.52 |
|  | 3 d | 0.55 ± 0.03 | 0.55 |
|  | 7 d | 0.32 ± 0.12 | 0.76 |
| 2a-03 (8) | 1 d | 1.61 ± 0.14 | 0.07 |
| (10 ug/ml) | 2 d | 1.55 ± 0.09 | 0.08 |
|  | 3 d | 1.24 ± 0.09 | 0.09 |
|  | 7 d | 0.79 ± 0.08 | 0.36 |
| 4a-02 (11)* | 1 d | 1.53 ± 0.27 | 0.11 |
| (10 ug/ml) | 2 d | 1.36 ± 0.13 | 0.20 |
|  | 3 d | 0.74 ± 0.08 | 0.46 |
|  | 7 d | 0.70 ± 0.05 | 0.48 |
| CELL | 1 d | 1.78 ± 0.07 | / |
|  | 2 d | 1.70 ± 0.12 | / |
|  | 3 d | 1.24 ± 0.13 | / |
|  | 7 d | 1.37 ± 0.07 | / |
| DMSO | 1 d | 1.70 ± 0.12 | 0.04 |
|  | 2 d | 1.68 ± 0.07 | 0.01 |

TABLE 4-continued

Effects on the proliferation of HepG2

| Group | Time | OD Value ($\bar{x} \pm s$) | Inhibition Rate |
|---|---|---|---|
|  | 3 d | 1.09 ± 0.07 | 0.12 |
|  | 7 d | 1.25 ± 0.19 | 0.08 |
| Ethanol | 1 d | 1.68 ± 0.07 | 0.05 |
|  | 2 d | 1.67 ± 0.05 | 0.01 |
|  | 3 d | 1.19 ± 0.07 | 0.03 |
|  | 7 d | 1.31 ± 0.09 | 0.04 |
| Fenretinide (DMSO) | 1 d | 1.61 ± 0.16 | 0.09 |
|  | 2 d | 1.37 ± 0.07 | 0.19 |
|  | 3 d | 1.07 ± 0.20 | 0.13 |
|  | 7 d | 1.17 ± 0.06 | 0.14 |
| Fenretinide (Ethanol) | 1 d | 1.67 ± 0.05 | 0.05 |
|  | 2 d | 1.31 ± 0.09 | 0.22 |
|  | 3 d | 1.06 ± 0.09 | 0.14 |

Finally, 3 more days are used as the action time for the subsequent experiment with MTT repeated twice, see Table 5.

TABLE 5

Effects on the Proliferation of HepG2

| Group | Concentration | OD Value ($\bar{x} \pm s$) | Inhibition Rate |
|---|---|---|---|
| Control Group |  | 2.167 ± 0.205 | 0.000 |
| DMSO |  | 1.849 ± 0.072 | 0.146 |
| Ethanol |  | 1.938 ± 0.123 | 0.105 |
| Fenretinide (DMSO) |  | 1.469 ± 0.078 | 0.322* |
| Fenretinide (Ethanol) |  | 1.422 ± 0.123 | 0.343* |
| 6a-02 (DMSO) | 10 ug/ml | 1.125 ± 0.146 | 0.480* |
| 3a-01 (DMSO) | 10 ug/ml | 0.978 ± 0.072 | 0.548* |
| 6a-01 (DMSO) | 10 ug/ml | 1.163 ± 0.102 | 0.463* |
| 3a-02 (DMSO) | 10 ug/ml | 1.331 ± 0.067 | 0.385* |
| 2a-03 (DMSO) | 10 ug/ml | 1.847 ± 0.091 | 0.468* |
| 4a-02 (Ethanol) | 10 ug/ml | 1.409 ± 0.090 | 0.349* |

*represents those meaningful in statistics for the comparison of the cell control groups.

It can be seen that the 6 drugs have better inhibition effect to liver cancer cells.

2.3 Effects on CEA Secretory Volume of A549 Cells The results are shown in Table 6; 6 ATRA derivatives (ditto) are selected for experiment with the drug concentration of 10 ug/ml for 3d to take the supernatant for the detection which indicates that these drugs have effects on CEA secretory volume.

TABLE 6

Effects on CEA Secretory Volume of A549 Cells

| Group | CEA (ug/L) |
|---|---|
| CONTROL | 5.8 |
| DMSO | 5.3 |
| Ethanol | 5.5 |
| Fenretinide (DMSO) | 4.5 |
| Fenretinide (Ethanol) | 4.3 |
| 6a-02 (DMSO) | 3.5 |
| 3a-01 (DMSO) | 2.9 |
| 6a-01 (DMSO) | 2.9 |
| 3a-02 (DMSO) | 2.8 |
| 2a-03 (Ethanol) | 3.9 |
| 4a-02 (DMSO) | 3.1 |

2.4 Effects on γ-GT Specific Activity and AFP Secretory Volume of HepG2 Cells

As shown in Table 7, 3a-01, 6a-01 and 4a-02 ATRA derivatives' effects on AFP secretory volume of liver cancer HepG2 cells are meaningful in statistics, and 6 drugs have effects of γ-GT secretory volume.

TABLE 7

Effects on γ-GT Specific Activity and AFP Secretory Volume of HepG2 Cells

| Group | AFP (ug/L) | γ-GT (U/L) |
| --- | --- | --- |
| CONTROL | 16.8 | 71.0 ± 1.0 |
| DMSO | 16.6 | 69.6 ± 2.1 |
| Ethanol | 16.5 | 69.0 ± 1.0 |
| Fenretinide (DMSO) | 15.1 | 66.6 ± 0.5 |
| Fenretinide (Ethanol) | 14.9 | 61.0 ± 1.0* |
| 6a-02 (DMSO) | 15.6 | 42.3 ± 2.0* |
| 3a-01 (DMSO) | 13.6* | 52.3 ± 1.5* |
| 6a-01 (DMSO) | 13.6* | 58.0 ± 1.5* |
| 3a-02 (DMSO) | 15.6 | 35.6 ± 1.0* |
| 2a-03 (DMSO) | 14.7 | 60.6 ± 0.5* |
| 4a-02 (Ethanol) | 10.4* | 32.6 ± 1.5* |

Compared with the control groups:
*P is less than 0.05.

2.5 Effects on Cell Cycle and Apoptosis of A549 Cells see Table 8

Seen from Table 8, 3a-02 most greatly effects on the apoptosis of A549 cells.

TABLE 8

Effects on cell cycle and apoptosis of A549 Cells

| Group | G0-G1 (%) | S (%) | G2-M (%) | Apoptosis Rate (%) |
| --- | --- | --- | --- | --- |
| Cell Control | 80.1 | 15.1 | 2.20 | 2.95 |
| Solvent Control (DMSO) | 66.3 | 25.7 | 2.66 | 5.83 |
| Solvent Control (Ethanol) | 67.9 | 22.9 | 2.92 | 6.47 |
| Fenretinide (DMSO) | 47.2 | 22.2 | 2.09 | 29.3 |
| Fenretinide (Ethanol) | 59.3 | 24.5 | 2.63 | 14.0 |
| 1 (6a-02) | 70.0 | 19.0 | 1.71 | 9.79 |
| 2 (3a-01) | 55.6 | 24.9 | 2.41 | 17.6 |
| 3 (6a-01) | 40.1 | 27.9 | 2.34 | 30.5 |
| 4 (3a-02) | 35.1 | 23.6 | 1.62 | 40.9 |
| 8 (2a-03) | 45.7 | 25.8 | 1.01 | 28.9 |
| 11 (4a-02) | 44.1 | 29.4 | 1.90 | 23.9 |

2.6 Effects on Cell Cycle and Apoptosis of HepG2 Cells see Table 9

Seen from Table 9, 4a-02 most greatly effects on the apoptosis of HepG2 cells.

TABLE 9

Effects on cell cycle and apoptosis of HepG2 Cells

| Group | G0-G1 (%) | S (%) | G2-M (%) | Apoptosis Rate (%) |
| --- | --- | --- | --- | --- |
| Cell Control | 68.8 | 17.8 | 5.90 | 7.68 |
| Solvent Control (DMSO) | 69.7 | 19.8 | 2.80 | 8.00 |
| Solvent Control (Ethanol) | 67.7 | 22.5 | 4.66 | 5.38 |
| Fenretinide (DMSO) | 67.3 | 19.8 | 7.64 | 5.71 |
| Fenretinide (Ethanol) | 60.0 | 24.1 | 5.69 | 10.6 |
| 1 (6a-02) | 57.5 | 25.4 | 2.61 | 15.7* |
| 2 (3a-01) | 56.3 | 24.8 | 4.14 | 16.5* |
| 3 (6a-01) | 57.4 | 26.7 | 5.30 | 11.1 |
| 4 (3a-02) | 40.3 | 27.9 | 2.71 | 30.2* |
| 8 (2a-03) | 57.3 | 25.5 | 3.40 | 16.3* |
| 11 (4a-02) | 30.9 | 28.5 | 3.20 | 38.1* |

Compared with the normal groups:
*P' is less than 0.005.

Figure 1:
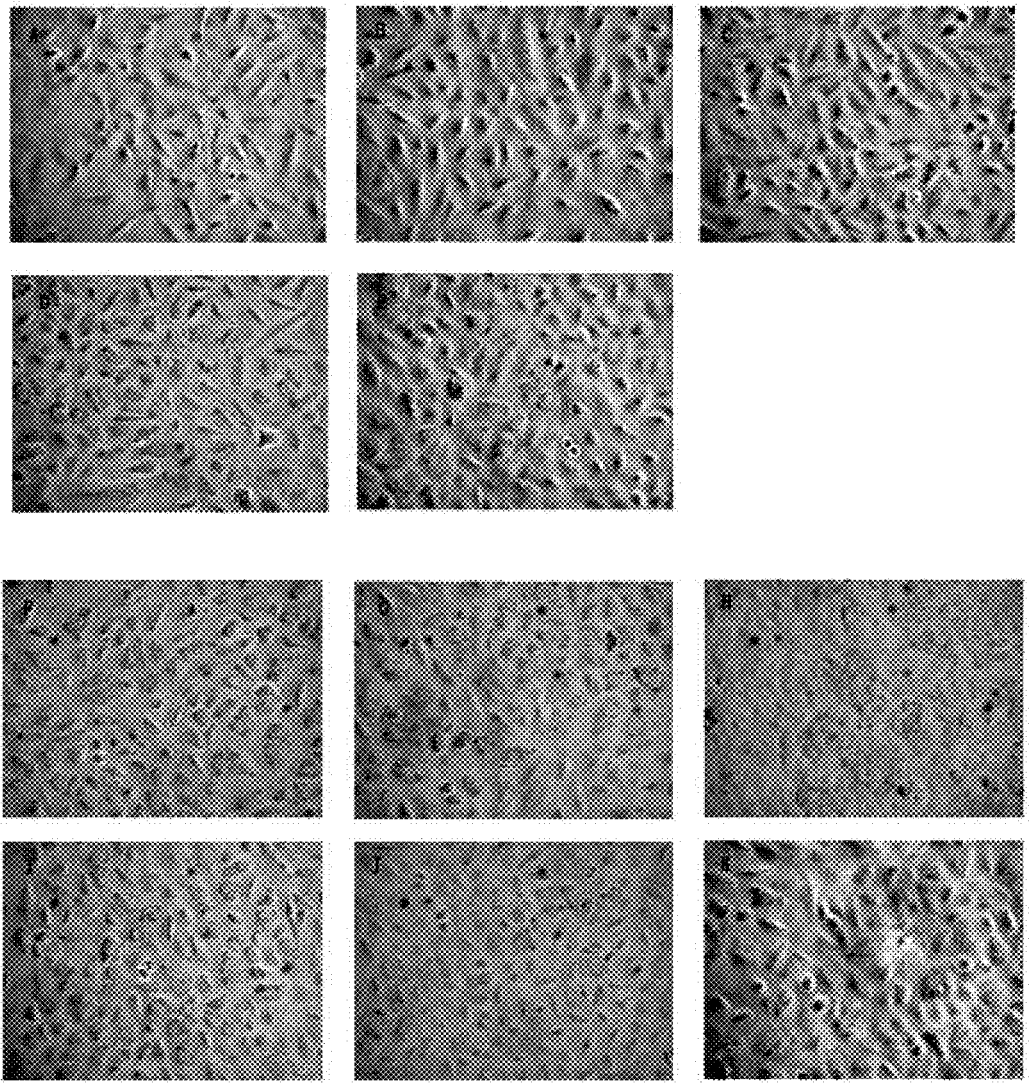
FIG. 1: A549 cell morphologic change (dosage of 10 ug/ml, 3 days)

2.7 Morphologic Change of A549 Cells (dosage of 10 ug/ml, 3 days) see FIG. 1

2.8 Hoechst33258 Staining Result of HepG2 Apoptosis see FIG. 2

Example 29

Determination of bioactivities of retinoid derivatives to leukemia cell strains K562 and NB4

Materials
1. Cell Strains
K562 cell strains are purchased from Shanghai Cell Library of CAS.
NB4 cell strains are presented by the Blood Internal Medicine Lab of No. 1 Affiliated Hospital of Anhui Medical University.
2. Reagents
Fenretinide and retinoid acid derivatives are synthesized by our lab.
Calf serum is purchased from the Hangzhou Sijiqing Biological Engineering Material Co., Ltd.
RPM11640 culture powder is from Gibco Company.
Wright's staining solution is from Hongci Medical Lab.
Propidium iodide (PI) is from Sigma Corp.
RNaseA is from Sigma Corp.
Fluorescence labelled monoclonal antibody including anti-human CD11b/PE, antibody, and corresponding homotype control antibody (IgGl/PE), are purchased from Coulter Immunotech (Paris, France).
3. Instruments
$CO_2$ Incubator: SHEL LAB
Super-clean bench: Suzhou Cleaning SW-CJ-1F type single double-face clean bench
Centrifuge: Sigma 3-16K
Flow cytometer: PICS XL-MCL
Oil immersion lens: COIC XSZ-H Experimental Method 1. Preparation
Retinoic acid derivatives and fenretinide are prepared as a storage solution of 10 mg/mL by anhydrous ethanol and stored at 20° C. and kept out of light.
2. Cell Culture
NB4 cells and K562 cells are inoculated with an initial concentration of $2*10^5$/ml in the RPMI1640 culture solution having 10% of calf serum (FBS), 100 u/ml of penicillin, 100 Lg/ml of streptomycin and 2 mmol/L of glutamine for suspension culture (37° C., 5% $CO_2$). Change the solution every 2-3 days.
3. Observation of Cellular Morphology
The cells above acted by the retinoic acid derivatives and fenretinide for 72 h are collected, centrifugated, smeared, naturally dried and stained by the Wright's staining solution. The cellular morphology is observed by an oil immersion lens.

4. Analysis of Cell Cycle

For the cells above acted by the retinoic acid derivatives and fenretinide (5 mg/mL) for 72 h, about $10^6$ of them are collected, washed by PBS twice, fixed by 70% of cold ethanol over 24 h, washed by PBS twice, added with 5 ug/ml of propidium iodide for staining and detected by a flow cytometer from which the data are analyzed and processed by the multi-cycle software.

5. Detection of Differentiation Antigen of Cells by Flow Cytometer

For the NB4 cells acted by the retinoic acid derivatives and fenretinide (5 mg/mL) for 72 h, $1*10^6$ of them are picked, washed by PBS twice, added with fluorescence labelled anti-human CD11b/PE antibody and corresponding homotype control antibodies to react with one another at the room temperature for 30 min, and washed by PBS once. Detect by the flow cytometer.

6 Results 6.1 Effects of Retinoic Acid Derivatives on Morphological Changes of Induction of Differentiation for Leukemia Cells The observation by the oil immersion lens shows that the morphologies of NB4 cells treated by the added retinoic acid derivatives are changed with diminished somas, reduced ratio of nucleus/plasma, increased granules in the plasma, and diminished, obviously recessed and twisted nucleus, similar to myelocyte and metamyelocyte (FIGS. 3 and 4).

6.2 Effects of Retinoic Acid Derivatives on Cell Cycle of Leukemia Cell Strains

The FCM analysis shows that, after the action of retinoic acid derivatives, the distribution of G1 phase is higher than that of the blank control groups, while the distribution of S phase is lower than that of the blank control groups. (Tables 9 and 10)

TABLE 9

Effects of Retinoic Acid Derivatives on Cell Cycle of NB4 Cells

| Group | G1 % | S % | G2 % |
|---|---|---|---|
| Blank Control | 47.01 | 51.46 | 1.53 |
| 6a-02 | 75.47 | 19.01 | 5.52 |
| 6a-01 | 38.24 | 59.06 | 2.70 |
| 4a-02 | 52.59 | 39.73 | 7.68 |
| 5a-02 | 60.06 | 35.03 | 4.91 |
| 4a-01 | 59.15 | 33.78 | 7.07 |
| 2a-03 | 65.72 | 28.74 | 5.54 |
| 3a-02 | 45.83 | 51.30 | 2.87 |
| 5a-01 | 59.28 | 35.74 | 4.98 |
| Fenretinide | 63.25 | 33.72 | 4.03 |

TABLE 10

Effects of Retinoic Acid Derivatives on Cell Cycle of K562 Cells

| Group | G1 % | S % | G2 % |
|---|---|---|---|
| Blank Control | 32.4 | 60.8 | 6.8 |
| 6a-02 | 32.2 | 56.8 | 10.9 |
| 6a-01 | 34.2 | 56.4 | 9.4 |
| 4a-02 | 33.1 | 55.4 | 11.5 |
| 5a-02 | 38.2 | 54.2 | 7.7 |
| 4a-01 | 39.1 | 53.9 | 6.9 |
| 2a-03 | 45.1 | 47.3 | 7.6 |
| 3a-02 | 39.7 | 54.2 | 6.0 |
| 5a-01 | 32.6 | 55.0 | 12.5 |
| 2a-02 | 35.4 | 54.6 | 9.9 |
| Fenretinide | 33.5 | 57.5 | 9.0 |
| 2a-01 | 36.1 | 51.4 | 12.5 |

6.3 Effects of Retinoic Acid Derivatives on the Surface Differentiation Antigen CD11b of NB4 Cells Treated by different retinoic acid derivatives for 72 h, the NB4 cells' CD11b expression is obviously increased in the comparison with the control groups. With the increase of CD11b expression, it shows that the NB4 cells are differentiated to the mature granular cells (FIG. 5).

The invention has been described according to the preferred examples. It shall be understood that the description and examples above are only used for explaining the invention by examples. In the premise of not deviating the spirit and scope of the invention, those skilled in the art can design multiple replacements and improvements from the invention, which shall fall within the protection scope of the invention.

What is claimed is:

1. A retinoid derivative of the formula (I),

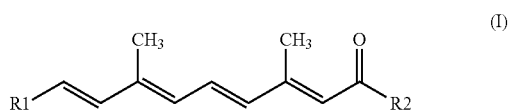

or an isomer, enantiomer, racemate, diastereomer mixture, racemic mixture, or pharmaceutically acceptable salt thereof, wherein: R1 represents a structure of formula (II) or formula (III), and R2 represents a structure of formula (IV),

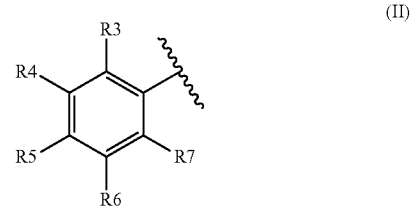

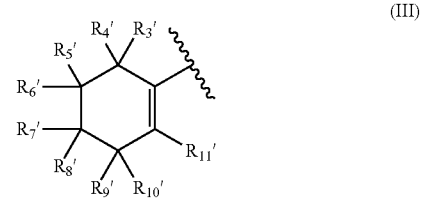

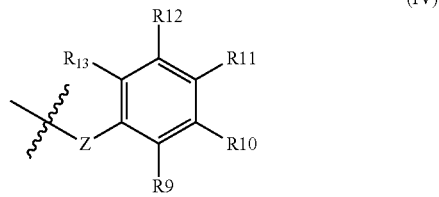

∿ represents bonding positions;

R3-R7 are same or different, each independently selected from hydrogen, nitro, halogen, amino, acyl, sulfonamide, carboxy, carboxylate, amide, nitrile, hydroxy, carbamyl, thiourea, aminomethyl, cyano, substituted or unsubstituted lower alkyl, substituted or unsubstituted lower alkenyl, substituted or unsubstituted lower alkynyl, substituted or unsubstituted lower alkoxy, substituted or unsubstituted lower alkylamino, substituted or unsubstituted lower alkylthio, substituted or unsubstituted lower alkylsulfo, substituted or unsubstituted lower alkylamide, substituted or unsubstituted lower aliphatic alkenyloxy, substituted or unsubstituted lower aliphatic alkynyloxy, substituted or unsubstituted aliphatic cycloalkyl, substituted or unsubstituted heterocycloalkyl, substituted or unsubstituted aryl, substituted or unsubstituted heteroaryl, substituted or unsubstituted aryloxy, substituted or unsubstituted heteroaryloxy, substituted or unsubstituted arylcarbonyl, substituted or unsubstituted heteroarylcarbonyl, substituted or unsubstituted aryloxycarbonyl, substituted or unsubstituted heteroaryloxycarbonyl, substituted or unsubstituted arylamino, substituted or unsubstituted heteroarylamino, substituted or unsubstituted arylthio, or substituted or unsubstituted heteroarylthio;

R3' and R4' are methyl, R5' to R10' are hydrogen, and R11' is methyl, R9-R13 are same or different, each independently selected from haloalkyl, haloalkoxy, hydrogen, nitro, halogen, amino, acyl, sulfonamide, carboxy, carboxylate, amide, nitrile, hydroxy, carbamyl, thiourea, aminomethyl, cyano, substituted or unsubstituted lower alkyl, substituted or unsubstituted lower alkenyl, substituted or unsubstituted lower alkynyl, substituted or unsubstituted lower alkoxy, substituted or unsubstituted lower alkylamino, substituted or unsubstituted lower alkylthio, substituted or unsubstituted lower alkylsulfo, substituted or unsubstituted lower alkylamide, substituted or unsubstituted lower aliphatic alkenyloxy, substituted or unsubstituted lower aliphatic alkynyloxy, substituted or unsubstituted aliphatic cycloalkyl, substituted or unsubstituted heterocycloalkyl, substituted or unsubstituted aryl, substituted or unsubstituted heteroaryl, substituted or unsubstituted aryloxy, substituted or unsubstituted heteroaryloxy, substituted or unsubstituted arylcarbonyl, substituted or unsubstituted heteroarylcarbonyl, substituted or unsubstituted aryloxycarbonyl, substituted or unsubstituted heteroaryloxycarbonyl, substituted or unsubstituted arylamino, substituted or unsubstituted heteroarylamino, substituted or unsubstituted arylthio, or substituted or unsubstituted heteroarylthio;

Z is O, S or NR14, R14 is selected from hydrogen, substituted or unsubstituted lower alkyl, substituted or unsubstituted lower alkenyl, substituted or unsubstituted lower alkynyl, substituted or unsubstituted aliphatic cycloalkyl, substituted or unsubstituted heterocycloalkyl, substituted or unsubstituted aryl, and substituted or unsubstituted heteroaryl; and the condition is that at least one of R9-R13 is haloalkyl or haloalkoxy.

2. The retinoid derivative according to claim 1, wherein: R3 and R7 are same or different, selected from substituted or unsubstituted lower alkyl, R4 and R6 are same or different, each selected from hydrogen, substituted or unsubstituted lower alkyl, substituted or unsubstituted lower alkoxy, substituted or unsubstituted lower aliphatic alkenyloxy, nitro, amino, lower alkyl substituted amino, substituted or unsubstituted N-heterocyclyl, and R5 is substituted or unsubstituted lower alkoxy; and the lower means containing 1-5 carbon atoms, and the substituents during the substitution are selected from nitro, halogen, amino, acyl, sulfonamide, carboxy, carboxylate, amide, nitrile, hydroxy, carbamyl, thiourea, aminomethyl or cyano.

3. The retinoid derivative according to claim 1, wherein R5 is methoxy and R6 is hydrogen, when R3, R7 and R4 are methyl.

4. The retinoid derivative according to claim 1, wherein R9, R10, R11, R12 and R13 are same or different, each independently selected from trifluoromethyl, trifluoromethoxy, hydrogen, halogen, hydroxyl, substituted or unsubstituted lower alkyl, substituted or unsubstituted lower alkoxy, substituted or unsubstituted lower aliphatic alkenyloxy, carboxylic acid, carboxylate, amide, nitrile, nitro, amino, substituted or unsubstituted lower alkyl substituted amino or N-heterocyclyl, provided that one of R9, R10, R11, R12 and R13 is trifluoromethyl or trifluoromethoxy.

5. The retinoid derivative according to claim 1, in the form of salts selected from hydrochloride, hydrobromide, napadisilate, phosphate, nitrate, sulfate, oxalate, tartrate, lactate, salicylate, benzoate, formate, acetate, propionate, valerate, diethylacetate, malonate, succinate, fumarate, pimelate, adipate, maleate, malate, sulfamate, phenpropionate, gluconate, ascorbate, isonicotinate, methanesulfonate, p-toluenesulfonate, citrate or amino acid salt.

6. The retinoid derivative according to claim 1, wherein said compound is selected from (4-trifluoromethylphenyl)-(all-trans)-3,7-dimethyl-9-(2,6,6-trimethyl-1-cyclohexen-1-yl)-2,4,6,8-nonatetraenoate;

(3-trifluoromethylphenyl)-(all-trans)-3,7-dimethyl-9-(2,6,6-trimethyl-1-cyclohexen-1-yl)-2,4,6,8-nonatetraenoate;

(2-trifluoromethylphenyl)-(all-trans)-3,7-dimethyl-9-(2,6,6-trimethyl-1-cyclohexen-1-yl)-2,4,6,8-nonatetraenoate;

(4-trifluoromethylphenyl)-(all-trans)-3,7-dimethyl-9-(2,6,6-trimethyl-1-cyclohexen-1-yl)-2,4,6,8-nonatetraenoic acid amide;

(3-trifluoromethylphenyl)-(all-trans)-3,7-dimethyl-9-(2,6,6-trimethyl-1-cyclohexen-1-yl)-2,4,6,8-nonatetraenoic acid amide;

(4-amino-3-trifluoromethylphenyl)-(all-trans)-3,7-dimethyl-9-(2,6,6-trimethyl-1-cyclohexen-1-yl)-2,4,6,8-nonatetraenoate;

(4-amino-2-trifluoromethylphenyl)-(all-trans)-3,7-dimethyl-9-(2,6,6-trimethyl-1-cyclohexen-1-yl)-2,4,6,8-nonatetraenoate;

(4-trifluoromethoxyphenyl)-(all-trans)-3,7-dimethyl-9-(2,6,6-trimethyl-1-cyclohexen-1-yl)-2,4,6,8-nonatetraenoate;

(3-trifluoromethoxyphenyl)-(all-trans)-3,7-dimethyl-9-(2,6,6-trimethyl-1-cyclohexen-1-yl)-2,4,6,8-nonatetraenoate;

(4-trifluoromethoxyphenyl)-(all-trans)-3,7-dimethyl-9-(2,6,6-trimethyl-1-cyclohexen-1-yl)-2,4,6,8-nonatetraenoic acid amide;

(3-trifluoromethoxyphenyl)-(all-trans)-3,7-dimethyl-9-(2,6,6-trimethyl-1-cyclohexen-1-yl)-2,4,6,8-nonatetraenoic acid amide;

(4-hydroxy-3-trifluoromethylphenyl)-(all-trans)-3,7-dimethyl-9-(2,6,6-trimethyl-1-cyclohexen-1-yl)-2,4,6,8-nonatetraenoic acid amide;

(4-hydroxy-2-trifluoromethylphenyl)-(all-trans)-3,7-dimethyl-9-(2,6,6-trimethyl-1-cyclohexen-1-yl)-2,4,6,8-nonatetraenoic acid amide;

(3-trifluoromethylphenyl)-(all-trans)-9-(4-methoxy-2,3,6-trimethylphenyl)-3,7-dimethyl-2,4,6,8-nonatetraenoate;

(2-trifluoromethylphenyl)-(all-trans)-9-(4-methoxy-2,3,6-trimethylphenyl)-3,7-dimethyl-2,4,6,8-nonatetraenoate;

(4-trifluoromethylphenyl)-(all-trans)-9-(4-methoxy-2,3,6-trimethylphenyl)-3,7-dimethyl-2,4,6,8-nonatetraenoate;

(3-trifluoromethoxyphenyl)-(all-trans)-9-(4-methoxy-2,3,6-trimethylphenyl)-3,7-dimethyl-2,4,6,8-nonatetraenoic acid amide;

(2-trifluoromethoxyphenyl)-(all-trans)-9-(4-methoxy-2,3,6-trimethylphenyl)-3,7-dimethyl-2,4,6,8-nonatetraenoic acid amide;

(4-amino-3-trifluoromethylphenyl)-(all-trans)-9-(4-methoxy-2,3,6-trimethylphenyl)-3,7-dimethyl-2,4,6,8-nonatetraenoate;

(4-amino-2-trifluoromethylphenyl)-(all-trans)-9-(4-methoxy-2,3,6-trimethylphenyl)-3,7-dimethyl-2,4,6,8-nonatetraenoate;

(4-trifluoromethoxyphenyl)-(all-trans)-9-(4-methoxy-2,3,6-trimethylphenyl)-3,7-dimethyl-2,4,6,8-nonatetraenoate;

(3-trifluoromethoxyphenyl)-(all-trans)-9-(4-methoxy-2,3,6-trimethylphenyl)-3,7-dimethyl-2,4,6,8-nonatetraenoate;

(3-trifluoromethoxyphenyl)-(all-trans)-9-(4-methoxy-2,3,6-trimethylphenyl)-3,7-dimethyl-2,4,6,8-nonatetraenoic acid amide;

(2-trifluoromethoxyphenyl)-(all-trans)-9-(4-methoxy-2,3,6-trimethylphenyl)-3,7-dimethyl-2,4,6,8-nonatetraenoic acid amide;

(4-trifluoromethoxyphenyl)-(all-trans)-9-(4-methoxy-2,3,6-trimethylphenyl)-3,7-dimethyl-2,4,6,8-nonatetraenoic acid amide;

(4-hydroxy-3-trifluoromethylphenyl)-(all-trans)-9-(4-methoxy-2,3,6-trimethylphenyl)-3,7-dimethyl-2,4,6,8-nonatetraenoic acid amide; or (4-hydroxy-2-trifluoromethylphenyl)-(all-trans)-9-(4-methoxy-2,3,6-trimethylphenyl)-3,7-dimethyl-2,4,6,8-nonatetraenoic acid amide.

7. A pharmaceutical composition, comprising a therapeutically effective amount of retinoid derivative according to claim 1 or an isomer, enantiomer, racemate, diastereomer mixture, racemic mixture, or pharmaceutically acceptable salt thereof as an active ingredient, and a pharmaceutically acceptable excipient.

8. A method of inhibiting hematological tumours, solid tumours and skin disorders in an individual comprising administering the individual an effective amount of retinoid derivative according to claim 1 or an isomer, enantiomer, racemate, diastereomer mixture, racemic mixture or pharmaceutically acceptable salt thereof.

\* \* \* \* \*